(12) United States Patent
Prabavathy et al.

(10) Patent No.: US 11,357,809 B2
(45) Date of Patent: Jun. 14, 2022

(54) **HERBAL PREPARATION FOR STIMULATION OF HAIR GROWTH, CONTROL OF HAIR FALL, DANDRUFF AND INFECTIONS THEREOF USING *AGERATUM* SPP**

(71) Applicant: GE Nutrients, Inc., Irvine, CA (US)

(72) Inventors: Vaiyapuri Ramalingam Prabavathy, Chennai (IN); Ramasamy Varadarajan Venkatesh, Hong Kong (CN); Jith Veeravalli, Irvine, CA (US)

(73) Assignee: GE Nutrients, Inc., Irvine, CA (US)

( * ) Notice: Subject to any disclaimer, the term of this patent is extended or adjusted under 35 U.S.C. 154(b) by 0 days.

(21) Appl. No.: 16/993,747

(22) Filed: Aug. 14, 2020

(65) Prior Publication Data

US 2021/0046138 A1 Feb. 18, 2021

Related U.S. Application Data

(60) Provisional application No. 62/886,573, filed on Aug. 14, 2019.

(51) Int. Cl.
| | | |
|---|---|---|
| *A61K 36/00* | (2006.01) | |
| *A61K 36/28* | (2006.01) | |
| *A61P 17/14* | (2006.01) | |
| *A61K 9/06* | (2006.01) | |
| *A61K 8/9789* | (2017.01) | |
| *A61Q 5/00* | (2006.01) | |
| *A61K 8/04* | (2006.01) | |
| *A61Q 7/00* | (2006.01) | |
| *A61K 45/06* | (2006.01) | |

(52) U.S. Cl.
CPC ............. *A61K 36/28* (2013.01); *A61K 8/042* (2013.01); *A61K 8/9789* (2017.08); *A61K 9/06* (2013.01); *A61P 17/14* (2018.01); *A61Q 5/006* (2013.01); *A61Q 7/00* (2013.01); *A61K 45/06* (2013.01); *A61K 2236/33* (2013.01)

(58) Field of Classification Search
CPC ............ A61P 17/14; A61Q 7/00; A61Q 5/006
See application file for complete search history.

(56) References Cited

U.S. PATENT DOCUMENTS

| | | |
|---|---|---|
| 2006/0018867 A1 | 1/2006 | Kawasaki |
| 2006/0165636 A1 | 7/2006 | Hasebe et al. |
| 2007/0122492 A1 | 5/2007 | Behr et al. |
| 2011/0311661 A1 | 12/2011 | Behr et al. |
| 2013/0316432 A1 | 11/2013 | Cyr |
| 2014/0271863 A1 | 9/2014 | Anderson et al. |

FOREIGN PATENT DOCUMENTS

| | | |
|---|---|---|
| CN | 106619362 A1 | 5/2017 |
| WO | 2014027370 A1 | 2/2014 |
| WO | WO-2014027370 A1 * | 2/2014 ............ A61K 8/368 |
| WO | 2017149490 A1 | 9/2017 |
| WO | 2018163192 A1 | 9/2018 |

OTHER PUBLICATIONS

Azzouni, F. et al. "The 5 Alpha-Reductase Isozyme Family: A Review of Basic Biology and Their Role in Human Diseases," Advances in Urology, vol. 2012, Article 1D530121, 18 pages (2012).
Bayne E.K. et al. "Immunohistochemical localization of types 1 and 2 5-alpha reductase in human scalp," Br J Dermatol Seo; 141(3): pp. 481-491 (1999).
Bayne, C. W. et al. "Serenoa repens (Permixon®): A 5a-reductase types I and II inhibitor: new evidence in a coculture model of BPH," The Prostate 40(4): pp. 232-241 (1999).
Bernard, F.-X. et al "Expression of type 1 5a-reductase and metabolism of testosterone in reconstructed human epidermis (SkinEthic®): a new model for creening skin-targeted androgen modulators," Int. J. Cosmet. Sci. 22(6):397-407 (2002).
Deloche, C. et al. "Histological features of peripilar signs associated with androgenetic alopecia," Arch Dermatol Res (2004) 295: 422-428.
Delos, S. et al. "Testosterone Metabolism in Primary Cultures of Human Prostate Epithelial Cells and Fibroblasts," J Steroid Biochem Mol Biol, 55(3-4): pp. 375-383 (1995).
Garza, L. et al. "Prostaglandin D2 Inhibits Hair Growth and is Elevated in Bald Scalp of Men with Androgenetic Alopecia," Science Translational Medicine vol. 4, Issue 126, 12 pages (2012).
Gautheron, P. et. al. "Bovine Corneal Opacity and Permeability Test: An In Vitro Assay of Ocular Irritancy" Fund. Appl. Toxicol. 18, pp. 442-449 (1992).
Gomella, L. G. "Chemoprevention using dutasteride: the REDUCE trial," Curr. Opin. Urol., 15(1):29-32 (2005).
Hamberg M et al. "On the metabolism of Prostaglandin E1 and E2 in man," J Biol Chem. 246: pp. 6713-6721 (1971).
Hanson, W R et al. "Subcutaneous or topical administration of 16,16 dimethyl prostaglandin E2 protects from radiation-induced alopecia in mice," Int J Radiat Oncol Biol Phys vol. 23: pp. 333-337 (1992).
Higuchi, R et al. "Kinetic PCR Analysis: Real-Time Monitoring of DNA Amplification Reactions," Biotechnology (NY);11(9):1026-30 (Sep. 1993).
Higuchi, R et al. "Simultaneous Amplification and Detection of Specific DNA Sequences," Biotechnology (NY) vol. 10: pp. 413-417 (Apr. 1992).
Ichikawa, A et al. "Molecular aspects of the structures and functions of the prostaglandin E receptors," J Lipid Mediat Cell Signal 14: pp. 83-87 (1996).

(Continued)

*Primary Examiner* — Qiuwen Mi
(74) *Attorney, Agent, or Firm* — Amin Talati Wasserman LLP; George M. Carrera, Jr.; Valerie Neymeyer-Tynkov

(57) ABSTRACT

This disclosure describes herbal preparations for the stimulation of hair growth, control of hair fall, control of dandruff, and control of dandruff-related infections thereof, using herbaceous plants, *Ageratum* spp. Processes for preparing the herbal preparations and methods for using them are also disclosed. Such an herbal preparation using plants, *Ageratum* spp. can be utilized as an efficient hair care solution in a wide range of hair growth related problems of humans in a cost-effective manner.

21 Claims, 9 Drawing Sheets

(56) References Cited

OTHER PUBLICATIONS

Johnstone, M A et al. "Prostaglandin-Induced Hair Growth," Survey of Ophthalmology, vol. 47(Suppl. 1):S185-S202 (Aug. 2002).
Lee, LG et al. "Allelic discrimination by nick-translation PCR with fluorogenic probes," Nucleic Acids Res 1993;21(16):3761-6.
Lehle, C. et al. "Human prostalic steroid 5 alpha-reductase isoforms—a comparative study of selective inhibitors," J Steroid Biochem Mol Biol, 54:(5-6) 273-9 (1995).
Livak, KJ et al. "Oligonucleotides with fluorescent dyes at opposite ends provide a quenched probe system useful for detecting PCR product and nucleic acid hybridization," PCR Methods and Applications;4(6): pp. 357-362 (1995).
Pradelles, P. et al. "Enzyme Immunoassay of Eicosanoids Using Acetylcholinesterase as Label: An Alternative to Radioimmunoassay," Anal. Chem. 57, pp. 1170-1173 (1985).
Messenger, A G. "The culture of dermal papilla cells from human hair follicles," Br J Dermatol 110: pp. 685-689 (1984).
Michelet, J F et al. "Activation of Cytoprotective Prostaglandin Synthase-1 by Minoxidil as a Possible Explanation for Its Hair Growth-Stimulating Effect," J Invest Dermatol: 108: pp. 205-209 (1997).
Philpott, M P et al. "Human hair growth in vitro," J Cell Sci 97: pp. 463-471 (1990).
Prager, N. et al. "A Randomized, Double-Blind, Placebo-Controlled Trial to Determine the Effectiveness of Botanically Derived Inhibitors of 5-alpha-Reductase in the Treatment of Androgenetic Alopecia," J Altern Complement Med., 8(2):143-52 (2002).
Rittmaster, R.S. "Finasteride," N. Engl. J. Med., vol. 330 No. 2:120-125 (1994).
Roenigk, H H, Jr. "New Topical Agents for Hair Growth," Clin Dermatol 1988: 6: pp. 119-121.
Santner, S.J. et al. "Comparative Rates of Androgen Production and Metabolism in Caucasian and Chinese Subjects," J Clin Endocrinol Metab, vol. 83 No 6, pp. 2104-2109 (1998).
Skalba, P. et al. "Content of 5-alpha-reductase (type 1 and type 2) mRNA in dermal papillae from the lower abdominal region in women with hirsutism," Clin Exp Dermatol. Jul.;31(4):564-70 (2006).
Soory, M., "Effects of the anti-androgen finasteride on 5a-reductase activity in human gingival fibroblasts in response to minocycline," J. Clin. Periodontol., 25(1):67-73 (1998).
Urade, Y et al. "Structural and functional significance of cysteine residues of glutathione-indipendent prostaglandin D synthase," J. Biol. Chem 270, 1422-1428 (1995).
Vanparys, Ph. et al. "Evaluation of the bovine opacity-permeability assay as an in vitro alternative to the Draize eye irritation test," Toxicol. In Vitro 7, pp. 471-476 (1993).
International Search Report and Written Opinion of the International Searching Authority issued in corresponding foreign application No. PCT/US20/46438, 10 pages (Jan. 12, 2021).
Agbafor, K.N. et al., "Analysis of Chemical Composition of Leaves and Roots of Ageratum conyzoides" Advances in Biological Research 9(6):397-400 (2015).
Enyinnaya, O.C. et al., "Impacts of Quarry Mining Activities on Herbaceous Plant *Ageratum conyzoides* L. in Ugwuele-Uturu, Abia State, Nigeria" Pakistan Journal of Biological Sciences 23:795-803 (2020).

* cited by examiner

HERBAL PREPARATION FOR STIMULATION OF HAIR GROWTH, CONTROL OF HAIR FALL, DANDRUFF AND INFECTIONS THEREOF USING *AGERATUM* SPP

CROSS-REFERENCE TO RELATED APPLICATIONS

This application claims the benefit of U.S. Provisional Patent Application No. 62/886,573, filed Aug. 14, 2019, which is incorporated by reference herein in its entirety.

FIELD OF THE INVENTION

This invention relates to the field of pharmaceutics, cosmetics and allied industries. Herbal preparations for stimulation of hair growth, control of hair fall, control of dandruff, and control of dandruff-related infections are described. Embodiments are particularly related to an herbal extraction process for preparing a hair growth stimulator using herbaceous plants, *Ageratum* spp. (for instance *Ageratum conyzoides* (Synonym: *Ageratum coeruleum*) and *Ageratum houstonianum*).

BACKGROUND

Hair loss/hair fall has become a ubiquitous affliction of human beings (both male and female gender) with the growing impact of global pollution and lifestyle changes. Most common reasons of radical or premature hair loss/hair fall are genetic predisposition, endocrine disorders, medication, radiation, chemotherapy, and exposure to chemicals, nutritional factors, generalized or local skin diseases, stress, child birth, Alopecia areata and mechanical damage such as Trichotillomania, hair styling treatment, hair braids and weaves.

In general, hair in humans is generated by the hair follicles embedded in the scalp. A healthy head of hair is said to contain between 100,000 and 150,000 hairs, and each hair within this head of hair possesses its own cycle. The life cycle of the hair can be described in three successive physiological phases such as, Anagen, Catagen and Telogen. Anagen is a phase of hair growth which may last from a few weeks to 10 years, Catagen phase is a transient phase of involution of the follicle and ceasing of hair growth with degeneration of the root which may last for a few weeks and Telogen is a phase of shedding of the hair with the root moving up towards the surface by lasting 1 to 5 months. At the end of Telogen phase, the hair therefore disappears from the scalp and this disappearance may extend from a few days to a few months before the follicle is reactivated to give a new hair in the Anagen phase.

Unfortunately, after a certain number of cycles, the follicle permanently ceases its production and the hair may be regarded as dead which may lead to baldness. As baldness progresses, there is a shift in the percentage of hair follicles in each phase with the majority shifting from Anagen to Telogen. The size of hair follicles is also known to decrease while the total number remains relatively constant. A variety of devices and procedures are adapted to stimulate hair follicles and re-generate hair growth in such cases. Most of the prior art approaches either employ a stimulator device or a drug for hair growth. One such common technique is hair transplantation. Briefly, plugs of skin containing hair are transplanted from areas of the scalp where hair was growing to bald or balding areas of the scalp. The transplantation technique can be a time-consuming and relatively costly affair. Other approaches include ultra-violet radiation and exercise therapy. While cosmetic aids are another significant approach for the stimulation of hair-growth, there is still a need in the art for compounds which may have greater stimulatory effect on hair growth.

Based on the foregoing a need exists for an improved herbal preparation for stimulation of hair growth, control of hair fall, dandruff and infections thereof using plants, *Ageratum* spp., as described in greater detail herein.

SUMMARY OF THE INVENTION

The following summary is provided to facilitate an understanding of some of the innovative features unique to the disclosed embodiment and is not intended to be a full description. A full appreciation of the various aspects of the embodiments disclosed herein can be gained by taking the entire specification, claims, drawings, and abstract as a whole.

It is, therefore, one aspect of the disclosed embodiments to provide an improved herbal extraction for stimulating hair growth.

It is another aspect of the disclosed embodiments to provide an improved process for extracting compounds of plants, *Ageratum* spp. (*Ageratum* species).

It is a further aspect of the disclosed embodiments to provide an improved herbal preparation for stimulation of hair growth, control of hair fall, dandruff and infections thereof using plants, *Ageratum* spp.

The aforementioned aspects and other objectives and advantages can now be achieved as described herein. An herbal preparation for stimulation of hair growth and control of hair fall, dandruff and infections thereof using herbaceous plants, *Ageratum* spp. (including *Ageratum conyzoides* (*Ageratum coeruleum*) and *Ageratum houstonianum*) is disclosed herein. At least one compound of plants, *Ageratum* spp. such as, N,N-bis(trimethylsilyl)-2-phenyl-7-(trifluoromethyl)quinolon-4-amine, 3',4',5,6,7,8-hexamethoxyflavone, Phytol, Precocene, Caryophyllene, Squalene, alpha-linolenic acid, 9,12-octadecadienoic acid (Z,Z)-, Hexadecanoic acid and Hydrocoumarin can be extracted utilizing a Common Plant Extraction Approach (CPEA). The extraction of compounds can be performed utilizing an ethanol solvent and a methanol solvent (i.e., alcoholic solvents) separately and the concentrated materials obtained at both the solvents are pooled together (or separately) in order to obtain an herbal extract for stimulating the follicles of the hair. The compounds of plants, *Ageratum* spp. in combination with an acceptable carrier or diluent can be further prepared into an herbal extract formulation such as, a liquid, oil or gel formulation for topical application. Such an herbal preparation using plants, *Ageratum* spp. can be utilized as an efficient hair care solution in a wide range of hair growth related problems of humans in a cost-effective manner. In an embodiment, an herbal preparation, herbal extract, herbal concentrated material, and/or herbal extract formulation of the present invention comprises, consists essentially of, or consists of, only compounds extracted from *Ageratum* spp. such as *Ageratum conyzoides*, and optionally residual extraction solvent and/or other chemicals used during the extraction process and/or for formulation purposes, such as an added carrier or diluent. An herbal extract of this invention prepared with ethanol as the extraction solvent is an ethanol herbal extract; similarly, if methanol was used as extraction solvent, the herbal extract is a methanol herbal extract. This nomenclature applies in view of the application of other extraction solvents, as well.

The Common Plant Extraction Approach (CPEA) described herein can be a principle extraction technique that is well known in the art for extracting the compounds of a plant. Initially, the leaves and soft stems of *Ageratum* spp. (preferably 60- to 90-days old plants) can be sliced into pieces (in an embodiment, approximately 1 cm wide and/or long; in another embodiment, with dimensions ranging from 0.1 cm to 10 cm, including for instance dimensions ranging from 0.1 cm to 3 cm, or 0.5 to 2 cm) and shade dried at room temperature. The sliced pieces can be also dried using a fluid flash dryer. Further, a mechanized pulverizing machine can be employed to grind the dried plant slices into coarse powder in order to thereby extract the compounds using the ethanol and methanol solvents separately. The solvent extraction process described herein can be performed for instance at a 1:10 (W/V) ratio using a soxhlet apparatus in order to thereby separate the green colored solvent extracts using a rotoevaporator.

The compounds obtained from both the ethanol solvent extraction process and the methanol solvent extraction process may be pooled together (or used separately) in order to form an herbal extract, that may be made into other herbal preparations such as an herbal concentrated material, herbal extract formulation, and/or other herbal preparation for stimulating hair growth.

The compounds extracted at the methanol solvent extraction process can be such as, for example, but not limited to, N,N-bis(trimethylsilyl)-2-phenyl-7-(trifluoromethyl)quinolon-4-amine, 1-deoxy-d-mannitol, 15-hydroxypentadecanoic acid, 2-chromenone, 3',4',5,6,7,8-hexamethoxyflavone, 3,5-di-tert-butyl benzoic acid, 3,7,11,15-tetramethylhexadec-2-en-1-ol, 4-tert-butyl-2,6-dimethylacetophenone, 6-vinyl-7-methoxy-2,2-dimethylchromene, Anhydro-d-mannosan, Beta-Funebrene, Caryophyllene, Coumarin, Hexa-o-methylmyricitin, Hydrocoumarin, Linoleoyl chloride, Methyl cis-11,14,17-icosatrienoate, Methyl linoleate, Neophytadiene, p-Octylacetophenone, Phenol, 2,4,6-tris(1,1-dimethylethyl), Phytol, Precocene I, and Squalene. In an embodiment, a methanol herbal extract of this invention includes all of the above, or at least one or more of the above.

The compounds extracted at the ethanol solvent extraction process can be such as, for example, but not limited to, N,N-bis(trimethylsilyl)-2-phenyl-7-(trifluoromethyl)quinolon-4-amine, (Z)-,Beta-farnesene, 1-(3,5-ditert-butyl-4-hydroxyphenyl)ethanone, 2-(1,3-benzodioxol-5-yl)-5-hydroxy-3,6,7,8-tetramethoxy-4h-chromen-4-one, 2-(3,4-dimethoxyphenyl)-5,6,7,8-tetramethoxy-4H-1-benzopyran-4-one, 2,4,6-tri-tert-butylphenol, 2-chromanone, 2H-chromen-2-one, 3',4',5,6,7,8-hexamethoxyflavone, 3,5-di-tert-butylbenzoic acid, 3,7,11,15-tetramethylhexadec-2-en-1-ol, 3-thujanol, 4-tert-butyl-2,6-d imethylacetophenone, 6-demethoxyageratochromene, 6-vinyl-7-methoxy-2,2-dimethylchromene, 9,12-octadecadienoic acid (Z,Z)-, All-trans-squalene, Alpha-benzopyrone, Alpha-caryophyllene, Alpha-linolenic acid, Alpha-tocopherol-P-D-mannoside, Beta-sesquiphellandrene, Butylphosphonic acid, hexyl 4-(2-phenylprop-2-yl)phenyl ester, Caryophyllene, Coumarin, Delta-cadinene, Dotriacontane, Gamma-mourolen, Gamma-sitosterol, Germacrene D, Gitoxigenin, Hexacosane, Hexadecanoic acid, Hydrocoumarin, Methyl cis-11,14,17-icosatrienoate, Methyl linoleate, Methyl palmitate, Neophytadiene, N-hexatriacontane, n-tertacontane, N-tetracosane, N-tetratriacontane, N-triacontane, Phytol, Precocene I, Precocene II, Squalene, Stigmasterol, Stimasta-4,2,2-dien-3,B-ol, and Tetracontane. In an embodiment, an ethanol herbal extract of this invention includes all of the above, or at least one or more of the above.

The solvents utilized for extracting compounds herein should not be construed in any limited sense. Those skilled in the art can understand that similar kind of solvents such as hexane, ethyl acetate, acetone, chloroform, dichloromethane, etc. can also used for preparing an herbal extract and preparing an herbal preparation that acts as a hair growth stimulant formulation of this invention. In an embodiment, the herbal extract is further formulated with an acceptable carrier or diluent in order to formulate as liquid, shampoo, oil or gel for topical application. The herbal extract can be dissolved in sterile distilled water (or for instance at 1-5 g/l) and the aqueous suspension can be filtered (through 1 to 5 um filter, pH adjusted to neutral) in order to form a liquid formulation of the herbal extract. Similarly, the herbal extract is dissolved in vegetable oil or PG/PL (propylene glycol/phospholipid) and the suspension is filtered (through 1 to 5 um filter) in order to form an oil formulation. The herbal extract can be dissolved in a small quantity of ethanol and filtered (through 1 to 5 um filter) in order to form the gel formulation. The mixture can be mixed vigorously using mechanized homogenizer to get the uniform gel product.

In an embodiment, the present invention is directed to an herbal preparation using herbaceous plants, *Ageratum* spp., comprising an herbal *Ageratum* spp. extract including at least one of N,N-bis(trimethylsilyl)-2-phenyl-7-(trifluoromethyl)quinolon-4-amine, 3',4',5,6,7,8-hexamethoxyflavone, Phytol, Precocene, Caryophyllene, and Squalene; and at least one of alpha-linolenic acid, 9,12-octadecadienoic acid (Z,Z)-, Hexadecanoic acid and Hydrocoumarin.

In an embodiment, *Ageratum* spp. is *Ageratum conyzoides* and/or *Ageratum houstonianum*. In an embodiment, ethanol is used as a solvent, preparing an ethanol herbal extract, and methanol is used as a solvent, preparing a methanol herbal extract. In an embodiment, the methanol extract comprises at least one of the following compounds: N,N-bis(trimethylsilyl)-2-phenyl-7-(trifluoromethyl)quinolon-4-amine, 1-deoxy-d-mannitol, 15-hydroxypentadecanoic acid, 2-chromenone, 3',4',5,6,7,8-hexamethoxyflavone, 3,5-di-tert-butylbenzoic acid, 3,7,11,15-tetramethylhexadec-2-en-1-ol, 4-tert-butyl-2,6-dimethylacetophenone, 6-vinyl-7-methoxy-2,2-dimethylchromene, Anhydro-d-mannosan, Beta-Funebrene, Caryophyllene, Coumarin, Hexa-o-methylmyricitin, Hydrocoumarin, Linoleoyl chloride, Methyl cis-11,14,17-icosatrienoate, Methyl linoleate, Neophytadiene, p-Octylacetophenone, Phenol, 2,4,6-tris(1,1-dimethylethyl), Phytol, Precocene I, and Squalene. In an embodiment the ethanol extract comprises at least one of the following compounds: N,N-bis(trimethylsilyl)-2-phenyl-7-(trifluoromethyl)quinolon-4-amine, (Z)-, Beta-farnesene, 1-(3,5-ditert-butyl-4-hydroxyphenyl)ethanone, 2-(1,3-benzodioxol-5-yl)-5-hydroxy-3,6,7,8-tetramethoxy-4h-chromen-4-one, 2-(3,4-dimethoxyphenyl)-5,6,7,8-tetramethoxy-4H-1-benzopyran-4-one, 2,4,6-tri-tert-butylphenol, 2-chromanone, 2H-chromen-2-one, 3',4',5,6,7,8-hexamethoxyflavone, 3,5-di-tert-butylbenzoic acid, 3,7,11,15-tetramethylhexadec-2-en-1-ol, 3-thujanol, 4-tert-butyl-2,6-dimethylacetophenone, 6-demethoxyageratochromene, 6-vinyl-7-methoxy-2,2-dimethylchromene, 9,12-octadecadienoic acid (Z,Z)-, All-trans-squalene, Alpha-benzopyrone, Alpha-caryophyllene, Alpha-linolenic acid, Alpha-tocopherol-p-D-mannoside, Beta-sesquiphellandrene, Butylphosphonic acid, hexyl 4-(2-phenylprop-2-yl)phenyl ester, Caryophyllene, Coumarin, Delta-cadinene, Dotriacontane, Gamma-mourolen, Gamma-sitosterol, Germacrene D, Gitoxigenin, Hexacosane, Hexadecanoic acid, Hydrocoumarin, Methyl cis-11,14,17-icosatrienoate, Methyl linoleate, Methyl palmitate, Neophytadiene, N-hexatriacontane, n-tertacontane, N-tetracosane, N-tetratriacontane, N-triacontane, Phytol, Precocene I, Precocene II, Squalene, Stigmasterol, Stimasta-4,2,2-dien-3,(3-ol, and Tetracontane.

In an embodiment, the herbal preparation comprises concentrated material from an ethanol herbal extract and a methanol herbal extract, and in an embodiment, the concentrated material comprises at least one of the following compounds from the methanol extract: N,N-bis(trimethylsilyl)-2-phenyl-7-(trifluoromethyl)quinolon-4-amine, 1-deoxy-d-mannitol, 15-hydroxypentadecanoic acid, 2-chromenone, 3',4',5,6,7,8-hexamethoxyflavone, 3,5-di-tert-butylbenzoic acid, 3,7,11,15-tetramethyl hexadec-2-en-1-ol, 4-tert-butyl-2,6-dimethylacetophenone, 6-vinyl-7-methoxy-2,2-dimethylchromene, Anhydro-d-mannosan, Beta-Funebrene, Caryophyllene, Coumarin, Hexa-o-methylmyricitin, Hydrocoumarin, Linoleoyl chloride, Methyl cis-11,14,17-icosatrienoate, Methyl linoleate, Neophytadiene, p-Octylacetophenone, Phenol, 2,4,6-tris(1,1-dimethylethyl), Phytol, Precocene I, and Squalene, and the concentrated material comprises at least one of the following compounds from the ethanol extract: N,N-bis(trimethylsilyl)-2-phenyl-7-(trifluoromethyl)quinolon-4-amine, (Z)-,Beta-farnesene, 1-(3,5-di-tert-butyl-4-hydroxyphenyl)ethanone, 2-(1,3-benzodioxol-5-yl)-5-hydroxy-3,6,7,8-tetramethoxy-4h-chromen-4-one, 2-(3,4-dimethoxyphenyl)-5,6,7,8-tetramethoxy-4H-1-benzopyran-4-one, 2,4,6-tri-tert-butylphenol, 2-chromanone, 2H-chromen-2-one, 3',4',5,6,7,8-hexamethoxyflavone, 3,5-di-tert-butylbenzoic acid, 3,7,11,15-tetramethylhexadec-2-en-1-ol, 3-thujanol, 4-tert-butyl-2,6-dimethylacetophenone, 6-deme, thoxyageratochromene, 6-vinyl-7-methoxy-2,2-dimethylchromene, 9,12-octadecadienoic acid (Z,Z)-, All-trans-squalene, Alpha-benzopyrone, Alpha-caryophyllene, Alpha-linolenic acid, Alpha-tocopherol-p-D-mannoside, Beta-sesquiphellandrene, Butylphosphonic acid, hexyl 4-(2-phenylprop-2-yl)phenyl ester, Caryophyllene, Coumarin, Delta-cadinene, Dotriacontane, Gamma-mourolen, Gamma-sitosterol, Germacrene D, Gitoxigenin, Hexacosane, Hexadecanoic acid, Hydrocoumarin, Methyl cis-11,14,17-icosatrienoate, Methyl linoleate, Methyl palmitate, Neophytadiene, N-hexatriacontane, n-tertacontane, N-tetracosane, N-tetratriacontane, N-triacontane, Phytol, Precocene I, Precocene II, Squalene, Stigmasterol, Stimasta-4,2,2-dien-3,(3-ol, and Tetracontane. In an embodiment, the pure herbal extract, concentrated material, is a liquid, powder, paste, or other form.

In an embodiment, the herbal preparation is an herbal extract formulation, further comprising a carrier and/or a diluent. In an embodiment, the formulation is an aqueous liquid formulation, an oil formulation, a gel formulation, or a shampoo.

In an embodiment, the present invention is directed to a process for preparing an herbal preparation containing *Ageratum* spp., comprising the steps of a. providing pieces of *Ageratum* spp., b. adding extraction solvent to the *Ageratum* spp. pieces to extract compounds from the pieces to prepare an herbal extract, c. removing the extraction solvent, and optionally removing the *Ageratum* pieces from the herbal extract to prepare concentrated material, and d. formulating the concentrated material into an herbal extract formulation. In an embodiment, the process further comprises pooling the herbal extract with a second herbal extract using a second solvent to prepare concentrated material. In an embodiment, the *Ageratum* spp. is *Ageratum conyzoides* and/or *Ageratum houstonianum*. In an embodiment, the *Ageratum* pieces are in powder form. In an embodiment, methanol and ethanol are used as solvents in the process, and said pooling step comprises pooling an ethanol herbal extract with a methanol herbal extract to prepare a concentrated material.

In an embodiment, the process includes formulating an herbal extract and/or concentrated materials by combining such with aqueous solution (and optionally filtering the resultant aqueous suspension) to prepare an aqueous liquid herbal extract formulation. The aqueous solution may be water.

In an embodiment, the process includes formulating an herbal extract and/or concentrated materials by dissolving the concentrated material in vegetable oil or propylene glycol/phospholipid and optionally filtering the resultant suspension to prepare an oil herbal extract formulation.

In an embodiment, the process includes formulating an herbal extract and/or concentrated materials by combining such with dissolving the concentrated material in a small quantity of ethanol in order to form a gel herbal extract formulation.

In an embodiment an herbal extract or concentrated material is formulated into a shampoo.

In an embodiment, an herbal preparation of *Ageratum* spp. according to this invention is prepared according to processes described throughout this application and in the claims.

In an embodiment, the present invention is directed to a method of stimulating hair growth, controlling hair fall, and/or controlling dandruff and associated infections in a subject, comprising the steps of a. providing an herbal preparation of *Ageratum* spp., and b. applying the herbal preparation to the external surface of the skin of the subject where hair growth, control of hair fall, or control of dandruff and related infections is desired. The external surface of the skin to which a composition of this invention is applied may have hair or may no longer have hair.

BRIEF DESCRIPTION OF THE DRAWINGS

The accompanying Figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

Herbal preparations using plants, *Ageratum* spp., for stimulation of hair growth, control of hair fall, control of dandruff, and control of dandruff-related infections are described. Herbal preparations according to this invention include an herbal extract, concentrated materials, an herbal extract formulation, and other related preparations. Herbal preparations of this invention can be utilized as an efficient hair care solution in a wide range of hair growth related problems of humans in a cost-effective manner.

References to a growth stimulation formulation and the like are not intended to be limiting, and refer to an herbal extract formulation of this invention unless indicated otherwise.

The particular values and configurations discussed in these non-limiting examples can be varied and are cited merely to illustrate at least one embodiment and are not intended to limit the scope thereof.

The embodiments now will be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

An herbal preparation of the present invention is prepared from *Ageratum* spp. In an embodiment, the herbal preparation is an extract of at least one of *Ageratum conyzoides* (also known as *Ageratum coeruleum*) and/or *Ageratum houstonianum*. In an embodiment, the herbal preparation is prepared from the leaves and/or soft stems of the *Ageratum* spp.

Figure 1:
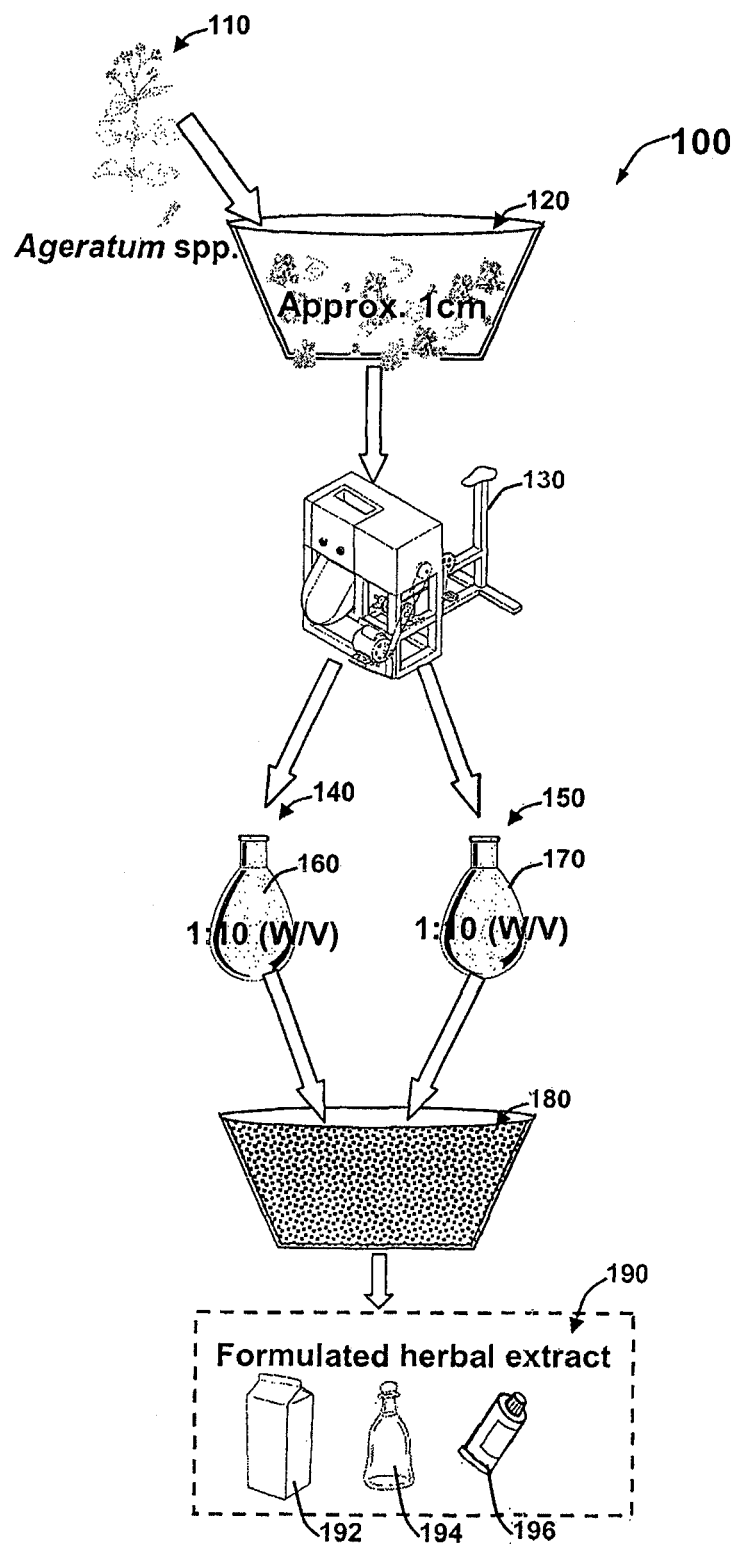
FIG. 1 is a perspective view of a process for preparing herbal preparations including herbal extracts, herbal concentrated materials, and herbal extract formulations using herbaceous plants, *Ageratum* spp., in accordance with the present invention and some disclosed embodiments.

FIG. 1 illustrates a perspective view of a process 100 for preparing herbal preparations of the present invention including herbal extracts 140-170, concentrated materials 180, and herbal extract formulations 190-196 using herbaceous plants, *Ageratum* spp. (including *Ageratum conyzoides*, (Synonym: *Ageratum coeruleum*) and *Ageratum houstonianum*) 110, in accordance with the disclosed embodiments. *Ageratum* spp. are annual herbaceous plants belonging to the family Asteraceae. They are common weeds and grow rapidly. They are known by several names such as goat weed, chick weed, white weed, etc. *Ageratum* spp. are found in many countries ranging from Southeastern North America to Central America, Asia and Africa; but the center of origin is in Central America and the Caribbean. *Ageratum* spp. are also found in several countries in tropical and sub-tropical regions, including India, Brazil, Vietnam, Nigeria, Kenya, Congo, Cameroon, etc. in abundance.

*Ageratum* spp. are very valuable herbs as they contain many bioactive compounds including flavonoids, alkaloids, cumarins, essential oils, chromenes, benzofurans, terpenoids, and tannins that have medicinal, antimicrobial, and insecticidal properties. The extracts of *Ageratum conyzoides* 110 and other *Ageratum* species have been used to cure a wide range of ailments such as muscle pains, inflammations, dysentery, indigestion, constipation, wounds in humans. The use of *Ageratum* spp. 110 in stimulation of hair follicles is novel. It has not hitherto been known that *Ageratum* spp. 110 have a stimulative action on hair growth and hair fall control.

A Common Plant Extraction Approach (CPEA) is adapted to prepare the herbal extract from *Ageratum* spp. 110. The Common Plant Extraction Approach (CPEA) described herein can be a principle extraction technique that is well known in the art for extracting the compounds 180 of plants. Note that other extraction processes can be alternatively employed in the place of suggested without losing the scope of invention. The leaves and soft stems of *Ageratum* spp. 110 preferably 60 to 90 days old plants are initially sliced into pieces 120 (e.g., approx. 1 cm) and in embodiment shade dried at room temperature (approx. 28-30° C.) for 48 hrs to 72 hrs. The sliced pieces 120 can be also dried at 45° C. using a fluid flash dryer for 24 hrs. Further, the dried plant slices 120 are ground to coarse powder using a mechanized pulverizing machine 130 in order to thereby extract the compounds 180 using the ethanol solvent 160, methanol solvent 170 and other solvents separately. The solvent extraction process described herein can in an embodiment be performed at a 1:10 (W/V) ratio using a soxhlet apparatus in order thereby to separate the green colored solvent extracts using a rotoevaporator. Note that the solvents utilized for extracting compounds herein should not be construed in any limited sense. Those skilled in the art can understand that similar kind of solvents such as hexane, ethyl acetate, acetone, chloroform, dichloromethane, etc. can also be used for preparing herbal extraction and developing the hair growth stimulant formulation. In an embodiment, said W/V ratio refers to the weight of the dried plant (W) and the volume of the solvent (V). In an embodiment, the W/V ratio is about 1:5 W/V to about 1:15 W/V, or about 1:7 W/V to about 1:15 W/V, or about 1:9 to about 1:11 W/V. These ratios are not intended as limiting.

The compounds extracted at the methanol solvent extraction process 150 can be such as, for example, but not limited to, N,N-bis(trimethylsilyl)-2-phenyl-7-(trifluoromethyl)quinolon-4-amine, 1-deoxy-d-mannitol, 15-hydroxypentadecanoic acid, 2-chromenone, 3',4',5,6,7,8-hexamethoxyflavone, 3,5-di-tert-butyl benzoic acid, 3,7,11,15-tetramethylhexadec-2-en-1-ol, 4-tert-butyl-2,6-dimethylacetophenone, 6-vinyl-7-methoxy-2,2-dimethylchromene, Anhydro-d-mannosan, Beta-Funebrene, Caryophyllene, Coumarin, Hexa-o-methylmyricitin, Hydrocoumarin, Linoleoyl chloride, Methyl cis-11,14,17-icosatrienoate, Methyl linoleate, Neophytadiene, p-Octylacetophenone, Phenol, 2,4,6-tris(1,1-dimethylethyl), Phytol, Precocene I and Squalene.

Table 1 below illustrates a list of compounds extracted by treating the plant material 120 using methanol as a solvent. This list is not intended as limiting.

TABLE 1

| # | Compound |
|---|---|
| 1 | N,N-bis(trimethylsilyl)-2-phenyl-7-(trifluoromethyl)quinolon-4-amine |
| 2 | 1-deoxy-d-mannitol |
| 3 | 15-hydroxypentadecanoic acid |
| 4 | 2-chromenone |
| 5 | 3',4',5,6,7,8-hexamethoxyflavone |
| 6 | 3,5-di-tert-butylbenzoic acid |
| 7 | 3,7,11,15-tetramethylhexadec-2-en-1-ol |
| 8 | 4-tert-butyl-2,6-dimethylacetophenone |
| 9 | 6-vinyl-7-methoxy-2,2-dimethylchromene |
| 10 | Anhydro-d-mannosan |
| 11 | Beta-Funebrene |
| 12 | Caryophyllene |
| 13 | Coumarin |
| 14 | Hexa-o-methylmyricitin |
| 15 | Hydrocoumarin |
| 16 | Linoleoyl chloride |
| 17 | Methyl cis-11,14,17-icosatrienoate |
| 18 | Methyl linoleate |
| 19 | Neophytadiene |
| 20 | p-Octylacetophenone |
| 21 | Phenol, 2,4,6-tris(1,1-dimethylethyl) |
| 22 | Phytol |
| 23 | Precocene I |
| 24 | Squalene |

Similarly, the compounds extracted at the ethanol solvent extraction process can be such as, for example, but not limited to, N,N-bis(trimethylsilyl)-2-phenyl-7-(trifluoromethyl)quinolon-4-amine, (Z)-Beta-farnesene, 1-(3,5-ditert-butyl-4-hydroxyphenyl)ethanone, 2-(1,3-benzodioxol-5-yl)-5-hydroxy-3,6,7,8-tetramethoxy-4h-chromen-4-one, 2-(3,4-dimethoxyphenyl)-5,6,7,8-tetramethoxy-4H-1-benzopyran-4-one, 2,4,6-tri-tert-butylphenol, 2-chromanone, 2H-chromen-2-one, 3',4',5,6,7,8-hexamethoxyflavone, 3,5-di-tert-butylbenzoic acid, 3,7,11,15-tetramethylhexadec-2-en-1-ol, 3-thujanol, 4-tert-butyl-2,6-dimethylacetophenone, 6-demethoxyageratochromene, 6-vinyl-7-methoxy-2,2-dimethylchromene, 9,12-octadecadienoic acid (Z,Z)-, All-trans-squalene, Alpha-benzopyrone, Alpha-caryophyllene, Alpha-linolenic acid, Alpha-octadecanoic acid, Alpha-tocopherol-P-D-mannoside, Beta-sesquiphellandrene, Butylphosphonic acid, hexyl 4-(2-phenylprop-2-yl)phenyl ester, Caryophyllene, Coumarin, Delta-cadinene, Dotriacontane, Gamma-mourolen, Gamma-sitosterol, Germacrene D, Gitoxigenin, Hexacosane, Hexadecanoic acid, Hydrocoumarin, Methyl cis-11,14,17-icosatrienoate, Methyl linoleate, Methyl palmitate, Neophytadiene, N-hexatriacontane, n-tertacontane, N-tetracosane, N-tetratriacontane, N-triacontane, Phytol, Precocene I, Precocene II, Squalene, Stigmasterol, Stimasta-4,2,2-dien-3,B-ol and Tetracontane, Tetradecanoic acid.

Table 2 below illustrates a list of compounds extracted by treating the plant material 120 using the ethanol solvent 170. This list is not intended as limiting.

TABLE 2

| # | Compound |
|---|---|
| 1 | N,N-bis(trimethylsilyl)-2-phenyl-7-(trifluoromethyl)quinolon-4-amine |
| 2 | (Z)-, Beta-farnesene |
| 3 | 1-(3,5-ditert-butyl-4-hydroxyphenyl)ethanone |
| 4 | 2-(1,3-benzodioxol-5-yl)-5-hydroxy-3,6,7,8-tetramethoxy-4h-chromen-4-one |
| 5 | 2-(3,4-dimethoxyphenyl)-5,6,7,8-tetramethoxy-4H-1-benzopyran-4-one |
| 6 | 2,4,6-tri-tert-butylphenol |
| 7 | 2-chromanone |
| 8 | 2H-chromen-2-one |
| 9 | 3',4',5,6,7,8-hexamethoxyflavone |
| 10 | 3,5-di-tert-butylbenzoic acid |
| 11 | 3,7,11,15-tetramethylhexadec-2-en-1-ol |
| 12 | 3-thujanol |
| 13 | 4-tert-butyl-2,6-dimethylacetophenone |
| 14 | 6-demethoxyageratochromene |
| 15 | 6-vinyl-7-methoxy-2,2-dimethylchromene |
| 16 | 9,12-octadecadienoic acid (Z,Z)- |
| 17 | All-trans-squalene |
| 18 | Alpha-benzopyrone |
| 19 | Alpha-caryophyllene |
| 20 | Alpha-linolenic acid |
| 21 | Alpha-octadecanoic acid |
| 22 | Alpha-tocopherol-β-D-mannoside |
| 23 | Beta-sesquiphellandrene |
| 24 | Butylphosphonic acid, hexyl 4-(2-phenylprop-2-yl)phenyl ester |
| 25 | Caryophyllene |
| 26 | Coumarin |
| 27 | Delta-cadinene |
| 28 | Dotriacontane |
| 29 | Gamma-mourolen |
| 30 | Gamma-sitosterol |
| 31 | Germacrene D |
| 32 | Gitoxrgenin |
| 33 | Hexacosane |
| 34 | Hexadeconpic acid |
| 35 | Hydrocoumarin |
| 36 | Methyl cis-11,14,17-icosatrienoate |
| 37 | Methyl linoleate |
| 38 | Methyl palmitate |
| 39 | Neophytadiene |
| 40 | N-hexatriacontane |
| 41 | n-tertacontane |
| 42 | N-tetracosane |
| 43 | N-tetratriacontane |
| 44 | N-triacontane |
| 45 | Phytol |
| 46 | Precocene I |
| 47 | Precocene II |
| 48 | Squalene |
| 49 | Stigmasterol |
| 50 | Stimasta-4,2,2-dien-3, β-ol |
| 51 | Tetracontane |
| 52 | Tetradecanoic acid |

The green colored solvent extract from ethanol/methanol/other solvents are in an embodiment removed using vacuum evaporation. Among the compounds of plants, *Ageratum* spp. at least four compounds, 9,12-octadecadienoic acid (Z,Z)-, Alpha-linolenic acid, Hexadecanoic acid, and Hydrocoumarin are identified as 5-alpha-reductase inhibitors. The 5-alpha-reductase enzyme metabolizes testosterone (known as the male hormone, although testosterone is also present in women) into dihydrotestosterone (DHT), which is known to induce scalp hair loss in man. Without being bound by theory, the 5-alpha-reductase inhibitors present in the extracts of *Ageratum* spp. can attach to the 5-alpha-reductase enzyme and prevent it from converting testosterone into DHT, thereby decreasing and stopping hair loss/hair fall.

Table 3 below illustrates the list of four compounds identified as 5-alpha-reductase inhibitors present in both ethanol and methanol extracts of the hair growth product. This list is not intended as limiting.

TABLE 3

| # | Compound |
|---|---|
| 1 | 9,12-octadecadienoic acid (Z,Z)- |
| 2 | α-linolenic acid |
| 3 | Hydrocoumarin |
| 4 | Hexadeconoic acid |

The compounds obtained at both the ethanol solvent extraction process 140 and the methanol solvent extraction process 150 (and other solvent processes) are further pooled together in order to form the pure herbal extract/concentrated materials 180 for stimulating the hair growth. The green colored solvent extracts are separated and the ethanol/methanol/other solvents are removed using vacuum evaporation. Among the compounds of plants, Ageratum spp. six major compounds, N,N-bis(trimethylsilyl)-2-phenyl-7-(trifluoromethyl)quinolon-4-amine, 3',4',5,6,7,8-hexamethoxyflavone, Phytol, Precocene, Caryophyllene, Squalene are identified as common components present in both ethanol and methanol extracts of the hair growth product. In an embodiment, an herbal preparation including an herbal extract, a pure herbal extract/concentrated material, and an herbal extract formulation of this invention includes one or more of these compounds, and in an embodiment, includes all of them.

Table 4 below illustrates the list of six major compounds identified as common components present in both ethanol and methanol extracts of the hair growth product. This list is not intended as limiting.

TABLE 4

| # | Compound |
|---|---|
| 1 | N,N-bis(trimethylsilyl)-2-phenyl-7-(trifluoromethyl)quinolon-4-amine |
| 2 | 3',4',5,6,7,8-hexamethoxyflavone |
| 3 | Phytol |
| 4 | Precocene |
| 5 | Caryophyllene |
| 6 | Squalene |

An herbal extract of this invention in an embodiment comprises the above 5-alpha-reductase inhibitors (listed in Table 3) and other major compounds of plants, Ageratum spp. 110 (listed in Table 4). An herbal extract in combination with an acceptable carrier or diluent can be further prepared into an herbal extract formulation 190 such as, aqueous (liquid), gel, oil or shampoo formulation for topical application. In an embodiment, an herbal extract formulation is applied to the scalp to stimulate hair growth, control hair fall, and control dandruff and related infections.

An herbal extract of Ageratum spp. alone or for instance as a concentrated material 180 with the above mentioned compounds can be dissolved in sterile distilled water (at 1-5 g/l) and the aqueous suspension can be filtered (for instance through 1 to 5 um filter, pH adjusted to neutral) in order to form a liquid formulation 192 of the herbal extract. Similarly, the herbal extract or concentrated material 180 can be dissolved in vegetable oil/PG/PL and the suspension then filtered (through 1 to 5 urn filter) in order to form an oil formulation 194. Also, the herbal extract or concentrated material 180 can be dissolved in a small quantity of ethanol and filtered (through 1 to 5 urn filter) in order to prepare a gel formulation 196. The mixture can be mixed vigorously using for instance a mechanized homogenizer to prepare the uniform gel product. Also, the herbal extract or concentrated material 180 can be dissolved in an acceptable carrier or diluent in order to prepare a shampoo formulation 190. The mixture can be mixed vigorously using mechanized homogenizer to prepare a uniform shampoo product. In an embodiment, methods of preparing gels, shampoos, aqueous and oil formulations may be used with an herbal extract of this invention. An herbal extract formulation 190 disclosed herein can be utilized to effectively control hair loss due to scenarios such as, but not limited to, genetic predisposition, endocrine disorders, medication, radiation, chemotherapy, exposure to chemicals, nutritional factors, generalized or local skin diseases, stress, child birth, Alopecia areata and mechanical damage, Trichotillomania, hair styling treatment, hair braids and weaves. An herbal extract formulation 190 of this invention, without being bound by theory, prevents the cessation of production of hair due to physiological phase changes such as, Anagen, Catagen and Telogen in humans.

Figure 2:
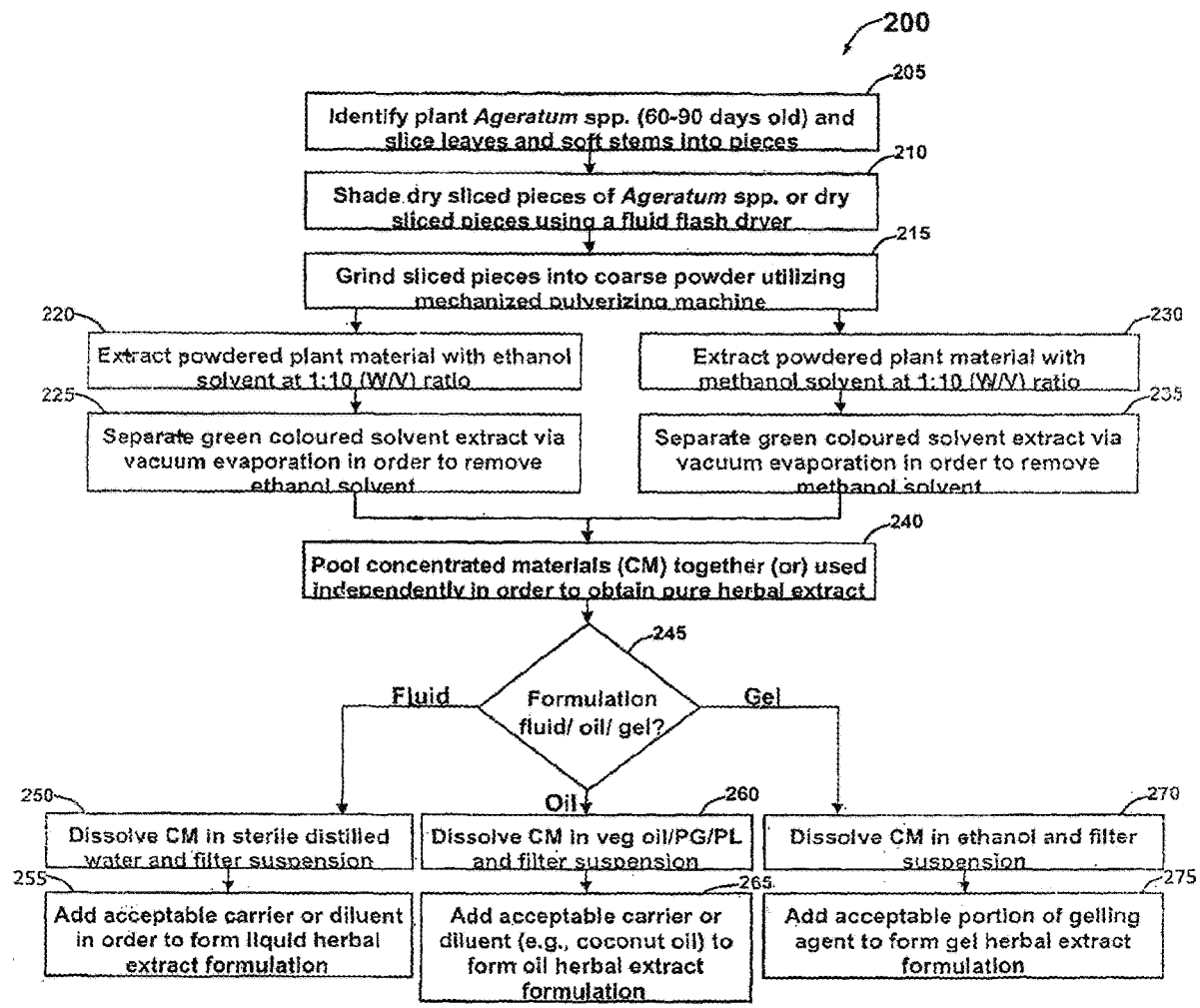
FIG. 2 is a high level flow chart of operations illustrating logical operational steps of a process for preparing herbal preparations of this invention including herbal extracts, herbal concentrated materials, and herbal extract formulations using herbaceous plants, *Ageratum* spp., in accordance with the present invention and some disclosed embodiments.

FIG. 2 illustrates a high level flow chart of operations illustrating logical operational steps of a method 200 for preparing an herbal extract formulation 190 using herbaceous plants, Ageratum spp. 110, in accordance with the disclosed embodiments. Note that in FIGS. 1-2, identical or similar blocks are generally indicated by identical reference numerals. Initially, the plants, Ageratum spp. 110 with 60 to 90 days of age can be identified and the leaves and soft stems of the Ageratum spp. 110 can be sliced into pieces (approx. 1 cm size) 120, as illustrated at block 205. The sliced pieces 120 of the plants, Ageratum spp. 110 can be further shade dried at room temperature or dried at 45° C. using a fluid flash dryer, as depicted at block 210. A mechanized pulverizing machine 130 can be employed to grind the dried plant slices 120 into coarse powder, as illustrated at block 215. The plant material can be further extracted using the ethanol and methanol solvents and other solvents 160 and 170 separately, as depicted at blocks 220 and 230. The solvent extraction process 140 and 150 described herein can be performed at a 1:10 (W/V) ratio using a soxhlet apparatus. The green colored solvents can be further extracted and separated by removing ethanol/methanol/other solvents 160 and 170 using a rotoevaporator, as illustrated at blocks 225 and 235.

The compounds obtained at both the ethanol solvent extraction process 140 and the methanol solvent extraction process 150 can be pooled together or separately in order to form the herbal extract 180 for stimulating hair growth, as depicted at block 240. As described earlier, six major compounds including N,N-bis(trimethylsilyl)-2-phenyl-7-(trifluoromethyl)quinolon-4-amine, 3',4',5,6,7,8-hexamethoxyflavone, Phytol, Precocene, Caryophyllene, Squalene are identified as common marker components in the hair growth product. Further, four compounds, a-linolenic acid, 9,12-octadecadienoic acid (Z,Z)-, Hexanoic acid and Hydrocoumarin are identified as 5-alpha-reductase inhibitors in the ethanol extract of Ageratum spp. and without being bound by theory these compounds are probably responsible or in part responsible for the hair loss-preventing activity of the hair growth herbal preparations of this invention. As illustrated at block 245, the concentrated herbal extract 180 can be further formulated with an acceptable carrier or diluent in order to be formulated as liquid, oil, gel or for instance shampoo for topical application. The purified form of herbal extract 180 can be dissolved in the sterile distilled water (at 1-5 g/l) in order to filter the aqueous suspension (through 1 to 5 um filter, pH adjusted to neutral), as illustrated at block 250. The concentrated material can be further added with acceptable carrier or diluent in order to form the aqueous (liquid) herbal extract formulation 192 of the herbal extract and/or concentrated materials, for instance as illustrated at block 255.

Similarly, the herbal extract 180 can be dissolved in vegetable oil/PG/PL in order to filter the suspension (through 1 to 5 um filter), as illustrated at block 260. The concentrated extract 180 can be further added with an acceptable carrier and diluent (e.g., coconut oil) in order to form the oil formulation 194, as depicted at block 265. The concentrated material 180 can be dissolved in a small quantity of ethanol in order to filter the suspension (through 1 to 5 um filter), as illustrated at block 270. The concentrated material 180 can be further added with the acceptable carrier and diluent in order to form the gel formulation 196, as depicted at block 275. The mixture can be mixed vigorously using mechanized homogenizer to get the uniform gel product 196. The concentrated material 180 can be further added with the acceptable carrier and diluent in order to form the shampoo formulation, as depicted at block 275. The mixture can be mixed vigorously using mechanized homogenizer to get the uniform shampoo product (not pictured). Note that the aqueous (liquid) 192, oil 194, gel 196, and shampoo (not pictured but part of 190) formulations of the herbal extracts are packed separately in PP (polypropylene) bottles aseptically. Such an herbal preparation using plants, *Ageratum* spp. can be utilized as an efficient hair care solution in a wide range of hair growth related problems of humans in a cost-effective manner.

In an embodiment, an *A. conyzoides* extract or other herbal preparation according to this invention may include the following characteristics: Appearance: brown powder. Odour: Characteristic. Identified or Identifiable by HPLC. Not less than 6% loss on drying. Saponins Content (gravimetry): Not less than 15.0% (w/w). Terpenes Content (gravimetry): Not less than 8%. Tannins Content (titration): Not less than 2.0%. Assay of marker compound HRF 028 by HPTLC: Not less than 0.75%. Assay of marker compound HRF 031 by HPTLC: Not less than 0.5%. Assay of marker compound HRF 058 by HPTLC: Not less than 0.1%. Assay of marker compound HRF 085 by HPTLC: Not less than 0.75%. Total Plate Count: maximum 10,000 cfu/g. Yeast and Mold: maximum 1000 cfu/g. Absent: *E. coli*, Colliform, *Salmonella*, *Pseudomonas aeruginosa*, *Staphylococcus aureus*. Total Heavy Metals: Not more than 10 ppm. Heavy Metals tested as per USP: Lead as Pb (Not more than 5 ppm); Cadmium as Cd (Not more than 1 ppm); Arsenic as As (Not more than 3 ppm); Mercury as Hg (Not more than 1 ppm).

In an embodiment, a subject of this invention is a mammal, including a mouse, rat, cat, dog, horse, and/or a human. The invention is useful for males and females. In an embodiment a herbal preparation of this invention is applied topically to the skin of the subject. Topical application may occur where hair is currently growing or where it is not currently growing on a subject's skin. In an embodiment, an effective amount of a preparation, extract, concentrated material, or formulation according to this invention is an amount sufficient to fully cover the area where stimulation of hair growth, control of hair fall, and/or control of dandruff and related infections is desired, with said desired effects. In an embodiment, an herbal extract formulation comprises at least 0.05 mg *A. conyzoides* extract or concentrated materials/ml formulation; in other embodiments, about 0.05-500 mg/ml, or 0.1-10 mg/ml; in other embodiments, about 1-100% *A. conyzoides* extract or concentrated materials, or for instance about 5%-20%. Without being bound by theory, the application of an herbal preparation according to this invention stimulates hair growth, controls hair fall, and/or controls dandruff and related infections by inhibiting 5-alpha-reductase type 1 gene and other mechanisms for instance as discussed in this application and as shown for instance in the Examples. In an embodiment, the present compositions may be used as a medicament for stimulating hair growth, controlling hair fall, and/or controlling dandruff and related infections. In an embodiment, an herbal preparation according to this invention may be used in the manufacture of a medicament to treat hair fall as discussed throughout this application, and/or in the manufacture of a medicament to stimulate hair growth, control hair fall, and/or control dandruff and related infections in a subject.

Clinical trials on formulations 190-196 have proved that the formulations do not have any adverse events and deviations. Under standard lab conditions, the formulations 190-196 did not indicate a potential for dermal irritation and/or allergic contact sensitization. See Example E, below.

Example A

In Vivo Experiments Showing Stimulation of Hair Growth and Fungal Control

Three different formulations—aqueous (liquid), gel, and oil—were prepared using the herbal preparation of *Ageratum* spp. and were tested for hair growth promotion in animal studies using C57BL/6 mice model. The experimental design is as follows:

| Group | Description |
| --- | --- |
| Group-I | Negative control |
| Group-II | Placebo - 1 (Gel excluding herbal extract) |
| Group-III | Placebo - 2 (Aqueous excluding herbal extract) |
| Group-IV | Placebo - 3 (Oil excluding herbal extract) |
| Group-V | Formulation -1 (Gel with *A. conyzoides* herbal extract) |
| Group-VI | Formulation - 2 (Aqueous with *A. conyzoides* herbal extract) |
| Group-VII | Formulation - 3 (Oil with *A. conyzoides* herbal extract) |
| Group-VIII | Standard Market Product (Positive Control) |

The hair growth potential of the above formulations was evaluated using C57BL/6 mice and for which, approval from ethical committee was obtained. Primary skin irritation test for all formulations was done for 48 hours. The hairs were removed from the mice using conventional method (Paraffin wax strip) and hair growth formulations were applied to the skin of the mice in regular intervals of 24 hours. The following are the observations made:

Colour change.
Raising of hair follicle.
Excision of skin for H & E staining.
Immuno-staining to differentiate the keratinocytes.
Hair density measurements.

Among the eight groups, Group I acted as a negative control and Group VIII acted as a positive control. The positive control group received (standard market product) as test compound according to the standard procedures. All the three formulations alone excluding the active principle were kept as Placebo (Group II, III, and IV). Hair depilation was made by paraffin wax strips. All the test formulations were applied at 24 hour intervals and the animals were kept under observation on changes in skin colour. Since the chosen mice displayed a change in the skin colour with reference to hair growth, the change of skin colour indicates the efficacy of the test formulations. It was observed that both Negative Control and Placebo Groups displayed normal hair growth profiles, whereas mice in the groups of V, VI, VII and VIII displayed advancement in hair growth patterns. The colouration from pink to grey and then to dark was significantly advanced in Group VII and it was comparable with Group VIII. Similarly, the H&E staining of sections also demonstrated the advancement in hair follicle regeneration and immunostaining has suggested early keratinization in test formulations and standard market product treated mice.

Interestingly, the hair density was maximum in Group VIII, followed by VII and V and the size of hair and hair bulb nature were also significantly changed in the above Groups as applied to mice compared to negative control and Placebo treated mice. Among the three formulations (gel, aqueous and oil), the gel and oil formulations were more effective than the aqueous formulation. Although the aqueous formulation induced localized hair growth profile, because of non-adherence to the skin, the expected results were not obtained. Overall, the study suggested, that the gel and oil formulations (Groups V and VII) displayed an effective hair growth profile comparable to that of the positive control (Group VIII), standard product.

Similarly, the 10% aqueous herbal extract prepared using *Ageratum* spp. was tested against dandruff causing fungal pathogens, *Pityrosporum ovale* and *Pityrosporum folliculitis* under in vitro conditions by well diffusion technique. The experimental design is as follows in Table 5.

TABLE 5

| Treatment | Description |
| --- | --- |
| 1 | Sterile water - Negative control) |
| 2 | Ketaconazole (100 ug/ml) - Positive control |
| 3 | Herbal extract (10% @ 50 ul/well) |
| 4 | Herbal extract (10% @ 100 ul/well) |

Agar plates were prepared and the dandruff pathogens, *Pityrosporum ovale* and *Pityrosporum* folliculitis were inoculated over the agar surface. Four wells were made using a sterile cork borer and 10% aqueous herbal extract of *A. conyzoides* was added at 50 and 100 pi in respective wells. Commercial fungicide, Ketaconazole at 100 ug/ml (Positive control) and sterile water (Negative control) were also added in respective wells. The plates were incubated at room temperature for seven days and observed for the inhibition of fungal growth.

Prominent zone of inhibition of both the dandruff pathogens, *P. ovale* and *P. folliculitis* was observed around aqueous herbal extract of *A. conyzoides* at 50 and 100 pi added wells and inhibition of fungal growth was higher than the commercial fungicide, Ketaconazole added well. No growth inhibition was recorded around sterile water added well. In summary, the study suggested that the aqueous herbal extract of *A. conyzoides* exhibited superior antifungal activity against the dandruff pathogens, *P. ovale* and *P. folliculitis* than the commercial antidandruff agent, Ketaconazole.

The following testing was performed using *Ageratum conyzoides* paste at various concentrations in vitro. *Ageratum conyzoides* paste is available from Gencor Pacific Ltd. (Hong Kong).

Example A1

Evaluation of *Ageratum conyzoides* on Activity Modulation of 5-alpha-reductase Type 1 Gene Expression in Fibroblasts SUMMARY: In this Example, 5-alpha-reductase type I gene expression in fibroblasts was decreased 4.5 times by a 0.1 mg/ml solution of *Ageratum conyzoides* extract, as compared to control.

Materials and Methods

Source Material: *Ageratum conyzoides* Extract; black paste. (Gencor Pacific, Hong Kong).

The *A. conyzoides* extract used in this Example included the following characteristics: Appearance: brown powder. Odour: Characteristic. Identified or Identifiable by HPLC. 4.7% loss on drying. Saponins Content (gravimetry): 16.3% (w/w). Terpenes Content (gravimetry): 8.8%. Tannins Content (titration): 2.3%. Assay of marker compound HRF 028 by HPTLC: 0.9%. Assay of marker compound HRF 031 by HPTLC: 0.8%. Assay of marker compound HRF 058 by HPTLC: 0.12%. Assay of marker compound HRF 085 by HPTLC: 0.8%. Total Plate Count: maximum 10,000 cfu/g. Yeast and Mold: maximum 1000 cfu/g. Absent: *E. coli*, Colliform, *Salmonella, Pseudomonas aeruginosa, Staphylococcus aureus*. Total Heavy Metals: Not more than 10 ppm. Heavy Metals tested as per USP: Lead as Pb (Not more than 5 ppm); Cadmium as Cd (Not more than 1 ppm); Arsenic as As (Not more than 3 ppm); Mercury as Hg (Not more than 1 ppm).

Positive Control Material: *Serenoa repens* Batch 065031 (Euromed S.A., Barcelona, Spain): clear yellow powder.

Cell culture: Murine fibroblasts (8alb/3T3 cells, clone A31), a clonal cell line derived from mouse, from ATCC (American Type Culture Collection, Manassas, Va.). This clone is derived from mouse embryonic fibroblasts obtained from Balb-c mouse embryo cultures (Aaronson and Todaro, 1968).

Study Design

In vitro methods are an alternative to traditional in vivo tests for evaluating biological properties of ingredients or finished products for cosmetic or biomedical use, for instance according to European cosmetic rules that ask manufacturers to assess product safety and effectiveness without employing animals.

The aim of this study is to point out and quantify changes in the expression of 5-alpha-reductase in a murine fibroblast cell line. 5-alpha-reductase is expressed in skin melanocytes, fibroblasts, and keratinocytes, and transforms testosterone into dihydrotestosterone, which as disclosed above is known to induce hair loss, and which is a key metabolite implicated in various skin disorders such as acne vulgaris, hirsutism, seborrhea, and androgenic alopecia. After birth, 5-alpha-reductase type I is expressed in more locations, including the liver, skin, scalp, and prostate. 5-alpha-reductase type 2 is expressed in prostate, seminal vesicles, epididymis, liver, and to a lesser extent the scalp and skin. As mentioned above, dihydrotestosterone is known to induce scalp hair loss in men. In this test, fibroblasts were pre-treated with testosterone in order to induce the production of 5-alpha-reductase and are subsequently treated with test substances or exposed to control substances for 48 hours. A titrated extract of *Serenoa repens* (Saw palmetto), a pharmacologically active substance used to treat prostate hyperplasia, is used as a positive control.

At the end of the 48-hour treatment period, analysis is performed by real time quantitative polymerase chain reaction (RT-qPCR), a sensitive and reliable method for the detection and quantitation of nucleic acid levels. Real-time PCR monitors the fluorescence emitted during the reaction as an indicator of amplicon production during each PCR cycle. (i.e. in real time) as opposed to endpoint detection.

Assay Procedures

Sample Preparation

For the test, the sample ("Test Sample") was solubilized directly in the Culture Medium at a concentration of 0.1 mg *Ageratum conyzoides* paste/ml Culture Medium and 0.025 mg *Ageratum conyzoides* paste/ml Culture Medium. Control samples also used the Culture Medium.

Culture Medium was made of Dulbecco's modified eagle's medium (DMEM), including penicillin-streptomycin, gentamycin, glutamine, and calf serum.

Fibroblast Cell Exposure to *Ageratum conyzoides* Extract

Fibroblast cells were seeded in 6-well plates for 24 hours at 100,000 cells/well. After that the cultures were treated for 24 hrs with 10 ng/ml testosterone. Fresh medium was added, supplemented with Test Samples having 0.1 ml/ml or 0.025 mg/ml *Ageratum conyzoides* extract. Untreated cells were used as negative control and cells treated with 10 μg/ml of *Serenoa repens* were used as positive control. Every sample was tested in duplicate. Fibroblast cells were exposed to the *Ageratum conyzoides* solution or a control solution for 48 hours.

RNA Extraction and Retro-Transcription

Total RNA was extracted from cells using a guanidium thiocyanate-based reagent according to standard protocol (TRIZOL, Invitrogen, Carlsbad Calif.). After precipitation and centrifugation (30 minutes at 12,000 rpm, 4° C.), RNA was resuspended in 20 μl sterile water and its concentration determined spectrophotometrically. 300 ng of total RNA were retrotranscribed into cDNA using random primers at 37° C. for 2 hours in a thermal cycler following the manufacturer's instructions. (Applied Biosystems, Foster City, Calif.)

Analysis of Gene Expression Profile by Quantitative Real-Time RT-qPCR

Figure 3:
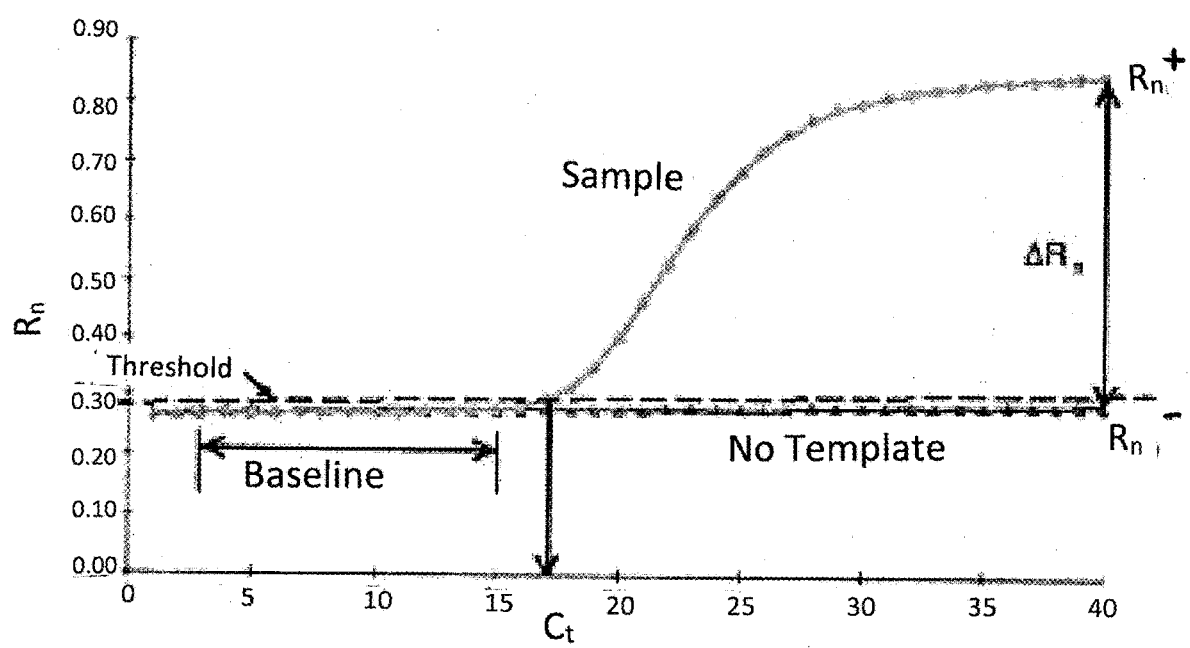
FIG. 3 is a graph showing a representative Real Time Quantitative Polymerase Chain Reaction amplification plot.

Changes in gene expression profile were analyzed by RT-qPCR technology using a SYBR-green based chemistry. Primer pair sequences for tyrosinase analysis were designed across intron-exon spanning regions and blasted against non-redundant database (GenBank) to verify the unicity of amplified region across the genome. This signal increases in direct proportion to the amount of PCR product in a reaction. By recording the amount of fluorescence emission at each cycle, it is possible to monitor the PCR reaction during an exponential phase where the first significant increase in the amount of PCR product correlates to the initial amount of target template. FIG. 3 shows a representative amplification plot and defines the terms used in the quantitation analysis. An amplification plot is the plot of fluorescence signal versus cycle number. In the initial cycles of PCR, there is little change in fluorescent signal. This defines the baseline for the amplification plot. An increase in fluorescence above the baseline indicates the detection of accumulated PCR product. A fixed fluorescence threshold can be set above the baseline. Briefly, the $C_t$ (cycle threshold) is defined as the number of cycles required for the fluorescent signal to cross the threshold (ie exceeds 10 fold the background level). $C_t$ levels are inversely proportional to the amount of target nucleic acid in the sample. So the higher the initial amount of the sample, the sooner accumulated product is detected in the PCR process as a significant increase in fluorescence, and the lower the $C_t$ value. $C_t$ values are very reproducible in replicates because the threshold is picked to be in the exponential phase of the PCR, where there is a linear relation between log of the change in fluorescence and cycle number and the reaction components are not limiting.

Comparative CT ($\Delta\Delta C_T$) Method for Relative Quantization of Gene Expression Changes in gene expression profile were measured using the comparative $C_T$ method ($\Delta\Delta C_T$ method). 28S ribosomal RNA was used as reference control for data normalization (normalizer). Briefly, the $\Delta\Delta C_T$ method enables relative quantization of template looking at expression levels relative to a normalizer. It is expected that the normalizer will have a higher expression level than the target (thus, a smaller $C_T$ value). The calculations for the quantization start with getting the difference ($\Delta C_T$) between the $C_T$ values of the target and the normalizer (EQUATION I).

$$\Delta C_T = C_T \text{ (target)} - C_T \text{ (normalizer)} \qquad \text{EQN. (I)}$$

This value is calculated for each sample to be quantitated; one of these samples should be chosen as the reference (control, untreated sample) for each comparison to be made. The comparative $\Delta\Delta C_T$ calculation involves finding the difference between each sample's $\Delta C_T$ and the control's $\Delta C_T$. If the control value is representing the minimum level of expression, and the experimental conditions are expected to increase the gene expression levels of the target gene, the $\Delta\Delta C_T$ values are expected to be negative (because the $\Delta C_T$ for the control sample will be the largest as it will have the greatest $C_T$ value). By contrast, if the experimental conditions are expected do decrease the expression levels of the target gene, the $\Delta\Delta C_T$ values will be positive ones (because the $\Delta C_T$ for the treated sample will be the largest as it will have the greatest $C_T$ value). The last step in quantization is to transform these values to fold changes according to the formula (EQUATION II).

$$\text{Fold change} = 2^{-\Delta\Delta C_T} \qquad \text{EQN. (II)}$$

Data Interpretation

In general, if the reduction is almost 2 times lower compared to the negative control (fold of reduction ≥2), the sample is considered effective in reducing 5-alpha-reductase expression.

Results and Discussion

Preliminary Cytotoxicity

The Test Sample (*Ageratum conyzoides* in medium, discussed above) showed an IC50 (concentration that caused 50% cell mortality) of 0.23 mg/ml. The concentrations used in the final test were: 0.1 mg/ml and 0.025 mg/ml.

Gene Expression Profile of 5-Alpha-Reductase Type 1

The gene expression profile of 5-alpha reductase was evaluated after 48 hours of treatment of fibroblast cells with 0.1 mg *Ageratum conyzoides* paste/ml and 0.025 mg *Ageratum conyzoides* paste/ml.

TABLE 6

Gene expression profiles of 5-alpha-reductase type 1

| | 48 hours | |
|---|---|---|
| Test Sample/Control | 5-alpha-reductase expression (DS) | Fold of reduction compared to Negative Control |
| 0.1 mg *A. conyzoides* extract/ml Culture Medium | 0.22 ± 0.08 | 4.5 (good reduction) |
| 0.025 mg *A. conyzoides* extract/ml Culture Medium | 0.88 ± 0.21 | 1.1 (no reduction) |

TABLE 6-continued

Gene expression profiles of 5-alpha-reductase type 1

| Test Sample/Control | 48 hours | |
|---|---|---|
| | 5-alpha-reductase expression (DS) | Fold of reduction compared to Negative Control |
| 10 ug S. repens/ ml Culture Medium (Positive Control) | 0.14 ± 0.05 | 7.1 |
| Negative Control (Culture Medium only) | 1 | — |

Figure 4:
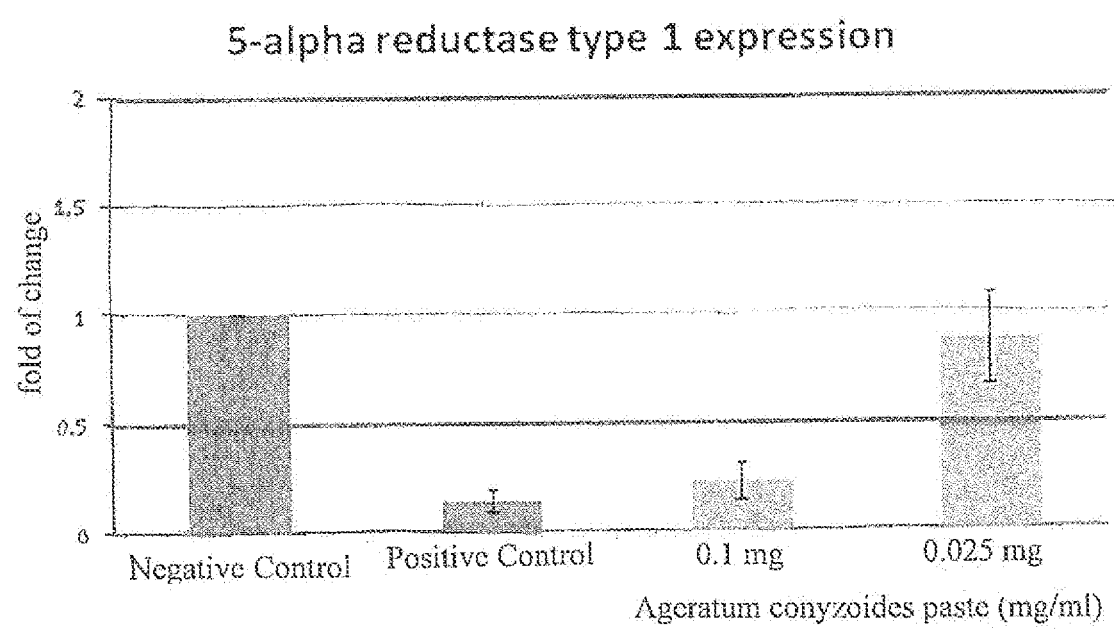
FIG. 4 is a graph showing the reduction of 5-alpha reductase type 1 expression in murine fibroblasts after treatment with a 0.1 mg/ml *Ageratum conyzoides* extract formulation according to this invention.

The data shown above and pictured in FIG. 4 shows that after 48 hours' exposure, the Test Sample reduced the expression of the 5-alpha-reductase type 1 gene compared with the negative (untreated) control in a dose-dependent manner. The highest effect was seen at the 0.1 mg/ml concentration, which showed 5-alpha-reductase gene expression reduced 4.5 times as compared with negative untreated controls, which was accorded an arbitrary gene expression level of 1.

Conclusion

In conclusion, *Ageratum conyzoides* paste was effective in reducing by 4.5 times the expression of messenger RNA codifying for the enzyme 5-alpha-reductase type 1 in murine fibroblasts, compared to untreated fibroblasts.

Example A2

Evaluation of *Ageratum conyzoides* on Activity Modulation of 5-alpha-reductase Type 1 Gene Expression in Human Hair Dermal Papilla Cells (HHDPC)

SUMMARY: In this Example, 5-alpha-reductase type I gene expression in human hair dermal papilla cells (HHDPC) having a fibroblast-like morphology was decreased 3.0 times by a 0.1 mg/ml solution of *Ageratum conyzoides* extract, as compared to control.

Materials and Methods

*Ageratum conyzoides* extract was used as a Source Material and *Serenoa repens* used as Positive Control Material, as described in Example A1.

Cell culture: Human hair dermal papilla cells (HHDPC) having a fibroblast-like morphology were used in this in vitro test system. (Human Hair Dermal Papilla Cells Reference P10881, Innoprot, Derio, Spain).

Study Design

The design of this study is similar to that described in Example A1, with the exception that HHDPCs having a fibroblast-like morphology were used instead of murine fibroblasts.

Assay Procedures

Sample Preparation

For this test, the *Ageratum conyzoides* extract ("Test Sample") was solubilized directly in Culture Medium at a concentration of 0.1 mg *Ageratum conyzoides* paste/ml Culture Medium and 0.025 mg *Ageratum conyzoides* paste/ ml Culture Medium. Control samples also used the Culture Medium. Culture Medium was made of Dulbecco's modified eagle's medium (DMEM), including penicillin-streptomycin, gentamycin, glutamine, and fetal bovine serum.

HHDPC Exposure to *Ageratum conyzoides* Extract

HHDPCs were seeded in 6-well plates for 24 hours at 14,000 cells/well. HHDPCs were then treated for 24 hrs with 10 ng/ml testosterone. Fresh medium was added, supplemented with Test Samples having 0.1 mg/ml and 0.025 mg/ml *Ageratum conyzoides* extract. Untreated cells were used as negative control and cells treated with 10 μg/ml of *Serenoa repens* were used as positive control. Every sample was tested in duplicate. HHDPCs were exposed to the *Ageratum conyzoides* extract or a control for 48 hours.

RNA extraction and retro-transcription, Analysis of gene expression profile by quantitative real-time RT-qPCR, Comparative CT ($\Delta\Delta C_T$) method for relative quantization of gene expression, and Data Interpretation were all performed as described in Example A1 above.

Results and Discussion

Preliminary Cytotoxicity Study

The Test Sample (*Ageratum conyzoides* in medium, discussed above) showed an IC50 (concentration that caused 50% cell mortality) of 0.23 mg/ml. The concentrations used in the final test were: 0.1 mg/ml and 0.025 mg/ml.

Gene Expression Profile of 5-alpha-reductase Type 1

The gene expression profile of 5-alpha reductase was evaluated after 48 hours of treatment of HHDPCs to 0.1 mg *Ageratum conyzoides* paste/ml and 0.025 mg *Ageratum conyzoides* paste/ml.

TABLE 7

Gene expression profiles of 5-alpha-reductase type 1

| Test Sample/Control | 48 hours | |
|---|---|---|
| | 5-alpha-reductase expression (DS) | Fold of reduction compared to Negative Control |
| 0.1 mg A. conyzoides extract/ml Culture Medium | 0.33 ± 0.08 | 3.0 (good reduction) |
| 0.025 mg A. conyzoides extract/ml Culture Medium | 1.36 ± 0.18 | <2 (no reduction) |
| 10 ug S. repens/ ml Culture Medium | 0.11 ± 0.05 | 7.1 |
| Negative Control (Culture Medium only) | 1 | — |

Figure 5:
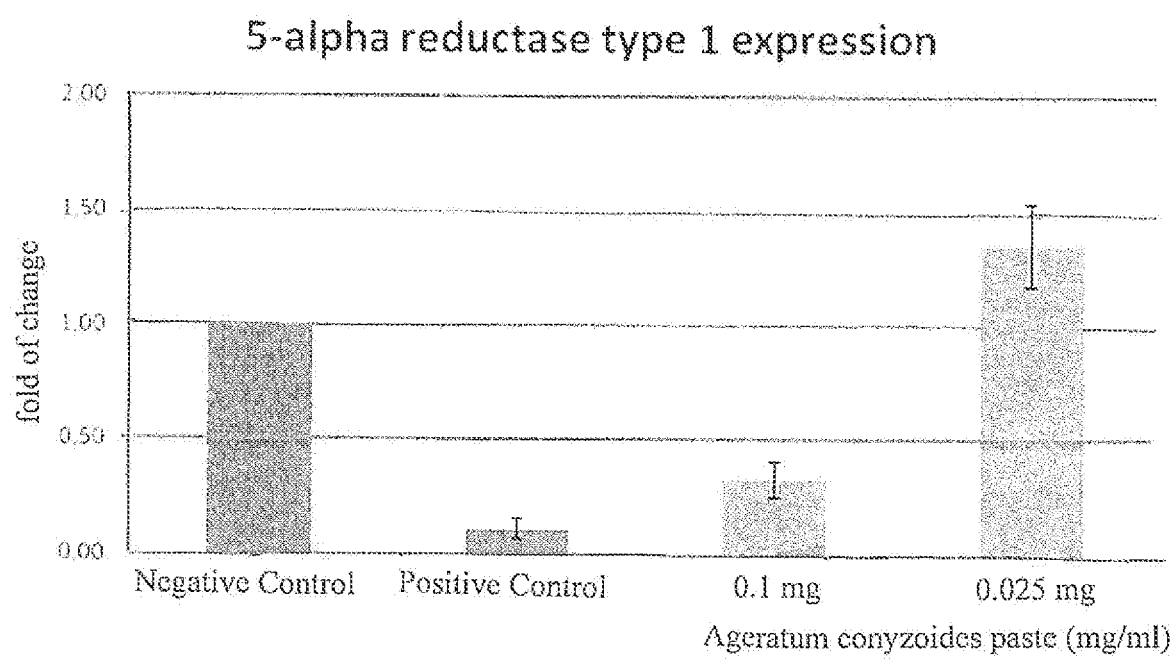
FIG. 5 is a graph showing the reduction of 5-alpha reductase type 1 expression in Human Hair Dermal Papilla Cells after treatment with a 0.1 mg/ml *Ageratum conyzoides* extract formulation according to this invention.

The data shown in Table 7 above and pictured in FIG. 5 shows that after 48 hours' exposure, the Test Sample reduced the expression of the 5-alpha-reductase type 1 gene compared with the negative (untreated) control in a dose-dependent manner. The highest effect was seen at the 0.1 mg/ml concentration, which showed 5-alpha-reductase gene expression reduced 3 times as compared with negative untreated controls, which was accorded an arbitrary gene expression level of 1.

Conclusion

In conclusion, *Ageratum conyzoides* paste was effective in reducing by 3.0 times the expression of messenger RNA codifying for the enzyme 5-alpha-reductase type 1 in HHDPCs, compared to untreated HHDPCs.

Example B1

Quantification of the Inhibitory Efficacy of *Ageratum conyzoides* Extract on Prostaglandin $D_2$ Production in Human Hair Dermal Papilla Cells (HHDPCs)

Summary

*A. conyzoides* extract inhibited Prostaglandin $D_2$ (PGD2) production in HHDPCs. 80.58% inhibition was observed by a 0.5 mg/ml *A. conyzoides* solution, and 78.27% inhibition by a 0.1 mg/ml solution.

Introduction

Prostaglandin D2 (PGD2) is a major prostaglandin produced mainly by mast cells. PGD2 performs several functions in the human body, including inflammatory modulation and vasodilation. It has important effects in recruiting eosinophils, basophils, and Th2 cells. Large amounts of PGD2 are also found in the human brain. Elevated levels of localized PGD2 have been linked to hair growth inhibition. High levels of topically applied PGD2 were demonstrated to inhibit hair growth, and the molecule was observed to reach much higher levels in balding scalp tissue than in non-balding tissue. PGD2 is also known to have an important role in asthma, and PGD2 blockers have been extensively researched to this purpose. Given the relevant role of PGD2 in several pathological processes, studying the mechanics of PGD2 expression and PGD2 synthase inhibition may be critical for therapeutic applications.

The dermal papilla is a highly active group of cells. It is derived from the dermis mesenchyme, located at the base of the hair follicle. The dermal papilla is implicated in controlling the hair growth cycle: dermal papilla cells are capable of inducing follicle development from the epidermis and the production of hair fibers. Early passage dermal papilla cells can induce hair growth in vivo.

Materials and Methods

*Ageratum conyzoides* extract used in this Example is as described in Example A1.

Cell Culture Methods and Media

HHDPCs were obtained from the European Collection of Authenticated Cell Cultures (ECACC; Public Health England, Salisbury, UK), and were preserved and cultured according to standard protocols.

HHDPCs were seeded in 24-well plates at 20,000 cells/well concentration, and cultured at 37° C., 95% humidity, 5% $CO_2$, using High Glucose Dulbecco's Modified Eagle's Medium (DMEM) containing 4.5 g/L D-glucose, 4 mM L-Glutamine, and supplemented with 10% fetal bovine serum, 1.2 g/L sodium bicarbonate and 0.1 mg/ml Penicillin, Streptomycin, and Kanamycin ("HHDPC Culture Medium"). Cell cultures were allowed to adhere and grow for 24 hours before the tests.

Preliminary Baseline PGD2 Quantification

In order to test the PGD2 baseline levels, untreated cells were plated as previously described and grown for 24 hours. Half the cell cultures were incubated for 6 hours with 0.05 mg/ml 2,2'-Azobis(2-methylpropionamidine) dihydrochloride, a known COX activator, in order to confirm the cells' response when stimulated to produce PGD2. Cell culture supernatant was removed, and the cells were detached and re-suspended in 0.1 M potassium phosphate. The cell solution was exposed to sonication for 25 min in order to obtain a cell lysate containing PGD2. The lysate was tested as a 1:10 dilution in EIA (Enzyme ImmunoAssay) buffer, showing an acceptable baseline production for the final test. The EIA test was performed according to the manufacturer's indications, and the readings were taken and analysed as reported below.

Test Sample Preparation and Final PGD2 Inhibition Assay

The sample (*Ageratum conyzoides* extract) was dissolved in complete HHDPC Culture Medium at a 5 mg/ml concentration (50 mg of the *A. conyzoides* extract was carefully weighed in a 15 ml sterile vial. 10 ml of complete HHDPC medium was added, to prepare the 5 mg/ml solution). Two sample dilutions (1:10 and 1:50 respectively) were prepared from this starting solution in order to prepare the final sample concentrations used in the tests.

The final PGD2 inhibition assay was performed on cell lysates, obtained as previously described from the following cell cultures:

Test Sample 1: 0.5 mg/ml *Ageratum conyzoides* extract paste dissolved in HHDPC Culture Medium;

Test Sample 2: 0.1 mg/ml *Ageratum conyzoides* extract paste dissolved in HHDPC Culture Medium;

Negative control: Untreated cell cultures (baseline PGD2 secretion).

All sample cultures were run in quadruple repeats.

Six hours before the test, the HHDPC cell cultures were treated with Test Samples 1 and 2. Untreated cultures were also used as a negative control. Two cultures from each sample were then used for PGD2 quantification, while the others were used for MTT (3-(4,5-dimethylthiazol-2-yl)-2,5-diphenyltetrazolium bromide) cell viability tests.

After the treatment with *A. conyzoides* Test Samples 1 and 2, the supernatant was removed, each culture was harvested and lysates were prepared. The samples obtained were diluted in EIA buffer (1:10 ratio).

The three samples obtained (from cells treated with Test Sample 1 (0.5 mg *A. conyzoides* extract/ml), Test Sample 2 (0.1 mg *A. conyzoides* extract/ml, and cells from untreated control) were then tested in the PGD2 competitive EIA assay together with standards containing known concentrations of PGD2 for comparison. After 18 hours' incubation, the samples and standards were exposed to Ellman's reagent and their absorbance at a 405 nm wavelength was read using a spectrophotometer (Tecan Sunrise, Tecan Group Ltd., Mannedorf, Switzerland). All the data were then corrected for blank readings, non-specific binding and baseline diluted-medium absorbance. The absorbance obtained from the standard was plotted vs. known concentration in order to identify a concentration-to-absorbance function, and the readings from the samples were tested through regression on a logistic-fit in order to determine the concentration of PGD2 contained in each supernatant.

Cell Viability Control

The remaining treated and untreated cell cultures were tested in order to verify that no cell viability alterations were caused by the sample, and therefore that the PGC2 quantification's results were unbiased by differences in cell concentrations.

In all cell cultures the HHDPC Culture Medium was replaced with fresh medium containing 1 mg/ml MTT (3-(4,5-dimethylthiazol-2-yl)-2,5-diphenyltetrazolium bromide). HHDPCs were then cultured at 37° C. for 1.5 hours. After incubation, the supernatant containing excess MTT was removed and the intercellular dye was extracted using isopropanol for 1 hour at room temperature on an orbital shaker. The extracted dye was read in triplicate using a spectrophotometer (Tecan Sunrise) at a measurement wavelength of 550 nm. Reference absorbance values at a 690 nm wavelength were subtracted in order to minimize non-specific noise. The corrected absorbance values were averaged and compared in order to evaluate the cell viability of treated cultures in comparison with the untreated control, as presented in Table 8 below.

Results and Discussion

Cell Viability Control

Figure 6:
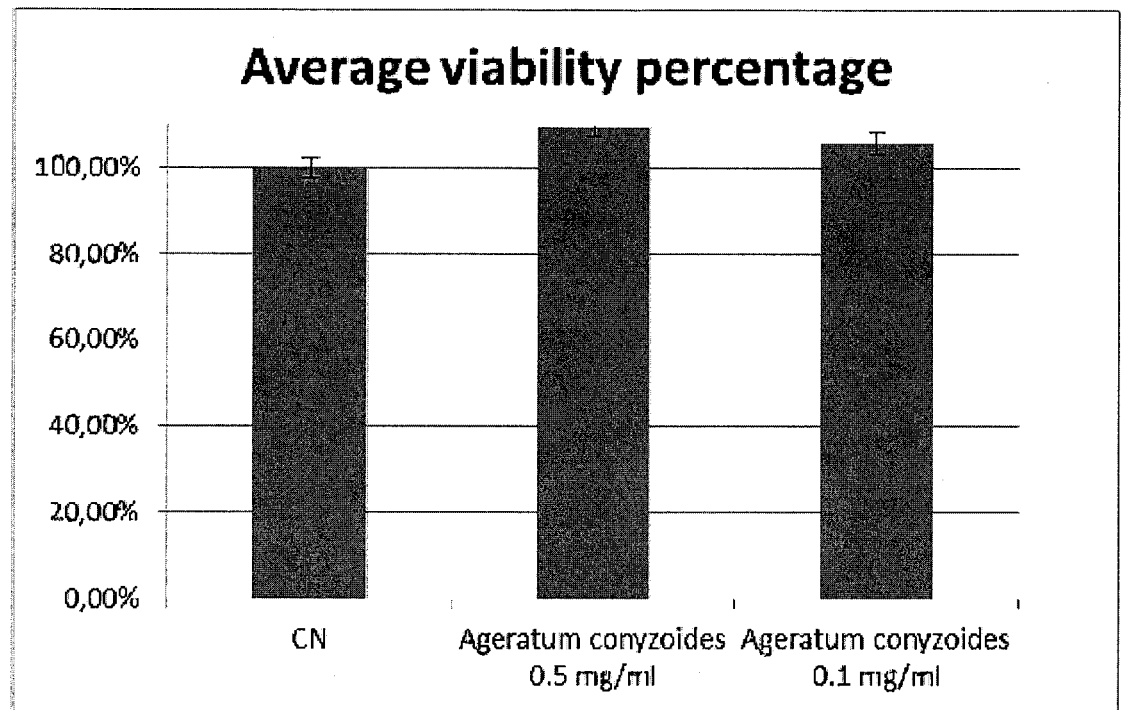
FIG. 6 is a graph showing *Ageratum conyzoides* extract of the present invention did not negatively impact the viability of HHDPCs in cell culture.

The Cell Viability of all the Tested Cultures was Assessed Using a Standard MTT Test. The Average percentage of cell viability was calculated in comparison with the untreated (negative) control. The results obtained showed all cultures presented optimal viability levels. HHDPC cultures treated with *A. conyzoides* extract were found to present a viability percentage of approximately 100% in comparison with the untreated (Negative) Control, as shown in Table 8 below and FIG. 6:

TABLE 8

Viability of HHDPCs in *A. conyzoides* extract solution
Average Cell Culture Viability

| Sample | Average (%) | Standard Deviation |
|---|---|---|
| Negative Control | 100.00% | 2.39% |
| *Ageratum conyzoides* extract (0.5 mg/ml) | 109.22% | 1.86% |
| *Ageratum conyzoides* extract (0.1 mg/ml) | 105.61% | 2.57% |

Data Analysis on the Inhibition of PGD2 Production

Baseline PGD2 production by untreated HHDPC cultures in the tested conditions was determined to be within the range of 1300-1600 pg PGD2/ml.

Figure 7:
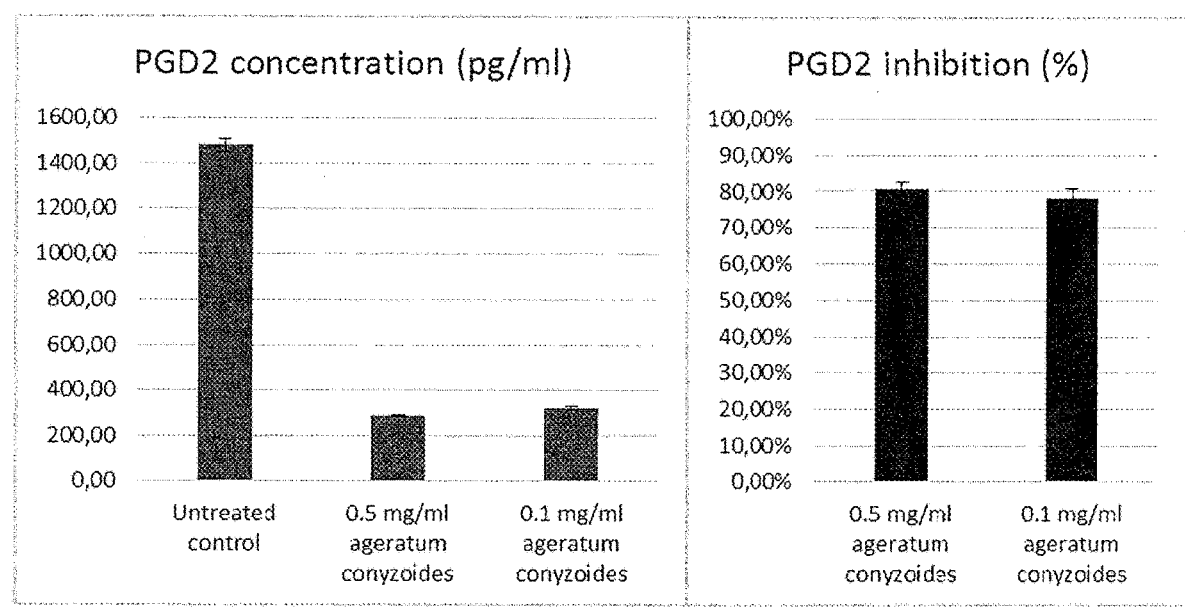
FIG. 7 is a graph showing a 78-80% decrease in PGD2 production in HHDPCs treated with an *Ageratum conyzoides* extract formulation according to this invention.

The average concentration of PGD2 in HHDPC medium after 18 hours' exposure to Test Sample or Negative Control was determined using the EIA PGD2 quantification assay, and standard deviation was calculated. The observed PGD2 inhibition results are reported in Table 9 below and shown in FIG. 7:

TABLE 9

Baseline PGD2 production by cultured HHDPCs and percentage of inhibition of PGD2 production by *A. conyzoides* extract

| Test Sample/Control | PGD2 concentration (pg/ml) | Inhibition percentage |
|---|---|---|
| Negative Control (Baseline PGD2 production) | 1478.99 ± 30.27 | — |
| Cells treated with Test Sample 1 (0.5 mg *A. conyzoides*/ml) | 287.18 ± 2.15 | 80.58% ± 2.19% |
| Cells treated with Test Sample 2 (0.1 mg *A. conyzoides*/ml) | 423.31 ± 8.61 | 78.27% ± 2.63% |

Conclusion

In conclusion, in accordance with the aforementioned experimental conditions, the 0.5 mg *A. conyzoides*/ml sample showed a reduction of PGD2 release by human hair dermal papilla cell cultures by 80.58%, and the 0.1 mg/ml sample showed a reduction of PGD2 release by human hair dermal papilla cell cultures by 78.27%.

Example B2

Quantification of the Inhibitory Efficacy of *Ageratum conyzoides* Extract on Prostaglandin $E_2$ Release in Human Hair Dermal Papilla Cells (HHDPCs)

Summary

*A. conyzoides* extract inhibited Prostaglandin $E_2$ (PGE2) release in HHDPCs. 51.54% inhibition was observed by a 0.5 mg/ml *A. conyzoides* solution, and 37.03% inhibition by a 0.1 mg/ml solution.

Introduction

Prostaglandin $E_2$ (PGE2) is an almost ubiquitous molecule that covers several functions in the human body, including inflammatory modulation and vasodilation. It has important effects in labour (softens cervix and causes uterine contraction) and also stimulates osteoblasts to release factors that stimulate bone reabsorption by osteoclasts. PGE2 is also the prostaglandin that ultimately induces fever. In human hair follicles, PGE2 has recently been described as one of the key modulators of hair growth. Indeed, topical application of PGE2 analogues was reported to increase human hair growth and to protect from radiation-induced alopecia. Trichogenic agents were also found to enhance prostaglandin endoperoxide synthase-1 (PGHS-1) activity, suggesting a link between prostaglandin synthesis and hair growth, as later confirmed by the role of PGHS-2 in the control of hair cycle.

The dermal papilla is a highly active group of cells. It is derived from the dermis mesenchyme, located at the base of the hair follicle. The dermal papilla is implicated in controlling the hair growth cycle: dermal papilla cells are capable of inducing follicle development from the epidermis and the production of hair fibers. Early passage dermal papilla cells can induce hair growth in vivo.

Materials and Methods

*Ageratum conyzoides* extract used in this Example is as described in Example A1.

HHDPC culture methods and media were as described in Example B1 above, and as follows:

HHDPCs were obtained from the European Collection of Authenticated Cell Cultures (ECACC; Public Health England, Salisbury, UK), and were preserved and cultured according to standard protocols.

HHDPCs were seeded in 24-well plates at 20,000 cells/well concentration, and cultured at 37° C., 95% humidity, 5% $CO_2$, using High Glucose Dulbecco's Modified Eagle's Medium (DMEM) containing 4.5 g/L D-glucose, 4 mM L-Glutamine, and supplemented with 10% fetal bovine serum, 1.2 g/L sodium bicarbonate and 0.1 mg/ml Penicillin, Streptomycin, and Kanamycin ("HHDPC Culture Medium"). Cell cultures were allowed to adhere and grow for 24 hours before the tests.

Preliminary Baseline PGE2 Quantification

In order to test PGE2 baseline levels, untreated cells were plated as previously described and grown for 24 hours. Half the cell cultures were incubated for 6 hours with 0.05 mg/ml 2,2'-Azobis(2-methylpropionamidine) dihydrochloride, a known COX activator, in order to confirm the cells' response when stimulated to produce PGE2. Cell culture supernatant was harvested and tested as a 1:10 dilution in EIA buffer, showing an acceptable baseline production for the final test. The EIA test was performed according to the manufacturer's indications (Cayman Chemical, Ann Arbor, Mich., US), and the readings were taken and analysed as reported below.

Test Sample Preparation and Final PGE2 Inhibition Assay

The sample (*Ageratum conyzoides* extract) was dissolved in complete HHDPC Culture Medium at a 5 mg/ml concentration (50 mg of the *A. conyzoides* extract was carefully weighed in a 15 ml sterile vial. 10 ml of complete HHDPC medium was added, to prepare the 5 mg/ml solution). Two sample dilutions (1:10 and 1:50 respectively) were prepared from this starting solution in order to prepare the final sample concentrations used in the tests.

The final PGE2 inhibition assay was performed using Human Hair Dermal Papilla Cells (HHDPC) cell cultures, which were grown as described above.

Test Sample 1: Cell cultures treated for 6 hours with 0.5 mg/ml *Ageratum conyzoides* extract paste dissolved in growth medium;

Test Sample 2: Cell cultures treated for 6 hours with 0.1 mg/ml *Ageratum conyzoides* extract paste dissolved in growth medium;

Negative Control: Untreated cell cultures (baseline PGE2 secretion).

All sample cultures were run in quadruple repeats.

Six hours before the test, the cell cultures were treated with 0.5 mg/ml or 0.1 mg/ml *Ageratum conyzoides* extract paste dissolved in culture medium. Untreated cultures were used as a negative control. Two cultures from each set were then used for PGE2 quantification, while the others were saved for MTT cell viability tests (see below).

After the exposure, the supernatant from each culture was harvested and diluted with EIA buffer (1:10 ratio). The three samples obtained (0.5 mg/ml, 0.1 mg/ml, and Negative Control) were then run in the PGE2 competitive EIA assay (Cayman Chemical, Ann Arbor, Mich., US) together with standards containing known concentrations of PGE2 for comparison.

After an 18-hour incubation period, the samples and standards were exposed to Ellman's reagent and their absorbance was read using a spectrophotometer (Tecan Sunrise, Tecan Group Ltd., Mannedorf, Switzerland) at a 405 nm wavelength. All the data were then corrected for blank readings, non-specific binding and baseline diluted-medium absorbance. The absorbance obtained from the standard was plotted vs. known concentration in order to identify a concentration-to-absorbance function, and the readings from the samples were tested through regression on a logistic-fit in order to determine the concentration of PGE2 contained in each supernatant.

MTT Cell Viability Control

The remaining treated and untreated cell cultures from each set (2 cultures treated with 0.5 mg/ml sample, 2 treated with 0.1 mg/ml sample, and 2 untreated Negative Control) were tested in order to verify that no cell viability alterations were caused by the sample, and therefore that the PGE2 quantification's results were unbiased by differences in cell concentrations.

All cell cultures were treated by replacing the growth medium with fresh one containing 1 mg/ml MTT and cultured at 37° C. for 1.5 hours. After incubation, the supernatant containing excess MTT was removed and the intercellular dye was extracted using isopropanol for 1 hour at room temperature on an orbital shaker. The extracted dye was read in triplicate using a spectrophotometer (Tecan Sunrise) at a measurement wavelength of 550 nm. Reference absorbance values at a 690 nm wavelength were subtracted in order to minimize non-specific noise. The corrected absorbance values were averaged and compared in order to evaluate the cell viability of treated cultures in comparison with the untreated control.

Results and Discussion

HHDPC viability in the presence of 0.5 mg *A. conyzoides*/ml, 0.1 0.5 mg *A. conyzoides*/ml, and Negative Control is as discussed in Example B1.

Data Analysis on the Inhibition of PGE2 Production

Figure 8:
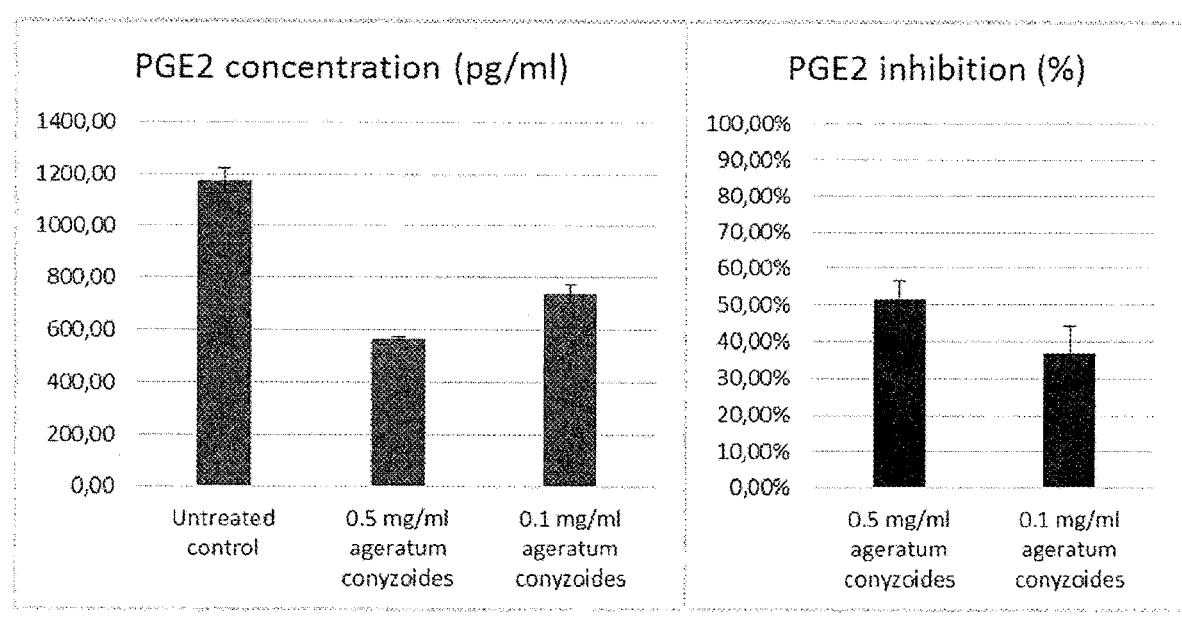
FIG. 8 is a graph showing a 37-52% decrease in PGE2 release in HHDPCs treated with an *Ageratum conyzoides* extract formulation according to this invention.

The preliminary quantification of Baseline PGE2 production by untreated HHDPC cultures under the tested conditions showed a concentration range of 1160-1260 pg/ml. During the final test, the average concentration for each sample was determined using the EIA PGE2 quantification assay, and standard deviation was calculated. The observed PGE2 inhibition of release results are reported in Table 10 and illustrated in FIG. 8:

TABLE 10

Baseline PGE2 production by cultured HHDPCs and percentage of inhibition of PGE2 production by *A. conyzoides* extract

| Test Sample/Control | PGE2 concentration (pg/ml) | Inhibition percentage |
|---|---|---|
| Negative Control (Baseline PGE2 production) | 1175.48 ± 49.59 | — |
| Cells treated with Test Sample 1 (0.5 mg *A. conyzoides*/ml) | 569.66 ± 7.02 | 51.54% ± 4.82% |
| Cells treated with Test Sample 2 (0.1 mg *A. conyzoides*/ml) | 740.25 ± 35.56 | 37.03% ± 7.24% |

Conclusion

In conclusion, Test Samples 1 and 2 ensured the promotion of hair follicle growth by *Ageratum conyzoides* extract according to this invention. The 0.5 mg *A. conyzoides*/ml sample (Test Sample 1) showed a reduction of PGE2 release by human hair dermal papilla cell cultures by 51.54%, and the 0.1 mg/ml sample (Test Sample 2) showed a reduction of PGE2 release by human hair dermal papilla cell cultures by 37.03%.

Example C

Assessment of Direct PGD2 Synthase Inhibition by *A. conyzoides* Extract

SUMMARY: The hair growth potential of a given formulation was evaluated using different in vitro studies and substantial evidence of promotion of hair growth by *Ageratum conyzoides* extract of this invention was established. In this study, *Ageratum conyzoides* extract according to this invention was assessed for its direct PGD synthase (PGDS) enzyme inhibition. *A. conyzoides* extract showed a very high inhibition of Lipocalin-Type PGD synthase, with 95.24% inhibition of the PGD synthase at a 1 mg/ml concentration of the *A. conyzoides* extract.

Introduction

Prostaglandin D2 (PGD2) is a major prostaglandin produced mainly by mast cells, and performs several functions in the human body including inflammatory modulation and vasodilation. PGD2 has important effects in recruiting eosinophils, basophils, and Th2 cells. Large amounts of PGD2 are found in the human brain.

PGD2 is produced through enzymatic alteration of its precursor PGH2 by Prostaglandin D2 synthase (PGDS). Two isoforms of the PGDS molecule are known: Hematopoietic-type PGDS (HPGDS) is widely distributed in the peripheral tissues and localized in antigen-presenting cells, mast cells, and megakaryocytes. Lipocalin-type PGDS (LPGDS) is localized in the central nervous system, in the male reproductive system, and in the human heart. Both enzymes produce PGD2 according to the following reaction in SCHEME 1.

SCHEME 1

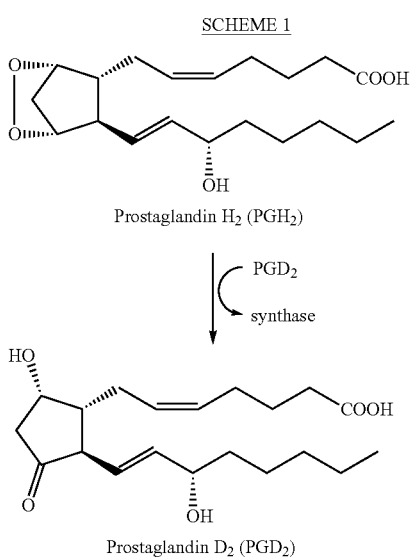

Prostaglandin H₂ (PGH₂)

↓ PGD₂ synthase

Prostaglandin D₂ (PGD₂)

Elevated levels of localized PGD2 have been linked to hair growth inhibition. High levels of topically applied PGD2 have been demonstrated to inhibit hair growth. PGD2 was observed to reach much higher levels in balding scalp tissue than in non-balding tissue. A corresponding increase in PGD2 Synthase (PGDS) expression was also observed.

PGD2 is also known to have an important role in asthma, and PGD2 blockers have been extensively researched to this purpose. Given the relevant role of PGD2 in several pathological processes, studying the mechanics of PGD2 expression and PGD2 synthase inhibition is critical for many therapeutic applications.

Materials and Methods

*Ageratum conyzoides* extract used in this Example is the paste as described in Example A1.

Assay Procedures

Step 1—Enzymatic Reactions

Direct enzymatic inhibition assessment was performed on both known types of PGDS (HPGDS and LPGDS). Known amounts of each enzyme and their substrates were used in a controlled in vitro reaction in order to produce PGD2. Each reaction tube was then analyzed separately in order to quantify any change in the amount of PGD2 produced in presence of a potential inhibitor. Any such change was measured in order to quantify the percentage of enzymatic inhibition induced by the samples.

The test protocol required setting up reaction mixes with LPGDS or HPGDS and required co-factors for the reactions (Glutathione for HPGDS, dithiothreitol for LPGDS) in a standard reaction buffer (0.1 M tris-HCl, pH 8.0). Separate reaction mixes were prepared to test the untreated reaction and several concentrations of potential inhibitor(s). Reactions were started by adding the enzymes' substrate, PGH2 (50 uM) and mixing. After 60 seconds, each reaction was stopped by adding 10% 1M HCl to each tube. Excess PGH2 could produce aspecific readings, and was therefore degraded using a light Iron (II) chloride solution. Once each required reaction was performed, the products were diluted to a fixed ratio (1:5000 for HPGDS, 1:2000 for LPGDS) and immediately tested for PDG2 quantification.

The following reactions were performed and tested:
(1) 100% HPGDS activity: Direct PHG2 to PGD2 conversion without any inhibitory agent.
(2) HPGDS inhibition: reaction in presence of the sample containing *A. conyzoides*. Inhibitory efficacy was tested on two separate concentrations of *A. conyzoides* (1 and 0.1 mg/ml respectively).
(3) 100% LPGDS activity: Direct PHG2 to PGD2 conversion without any inhibitory agent.
(4) LPGDS inhibition: reaction in presence of the sample containing *A. conyzoides*. Inhibitory efficacy was tested on two separate concentrations of *A. conyzoides* (1 and 0.1 mg/ml respectively).
(5) Negative Control: Background tubes were set using the same substrates and solutions of the previous reactions without adding the enzyme. Readings from the background tubes were subtracted from the corresponding enzymatic reaction.

Step 2—Enzyme-Immunoassay (EIA) Quantification of PGD Synthase Products

Enzyme-immunoassays were conducted to quantify synthase products. PGD2 quantification was performed using a standard competitive enzyme immunoassay kit (Cayman Chemical, Ann Arbor, Mich., US). The product from each reaction was quantified in a competitive reaction vs. acetylcholinesterase-linked PGD2. A standard curve was also tested using 8 progressive 1:2 dilutions of PGD2 starting from a 15 ng/ml solution. 50 ml each of products from the previously performed enzymatic reactions were tested separately. The samples were incubated for two hours at room temperature and exposed to Ellman's reagent, which reacts to the tracer producing a yellow dye (5-thio-2-nitrobenzoic acid). The absorbance generated by the dye in each sample and standard was measured using a spectrophotometer (Tecan Sunrise) at 405 nm wavelength. Each absorbance value was corrected for baseline absorbance (blank subtraction) and for non-specific binding (a NSB solution was prepared and tested, and the resulting absorbance was subtracted from each other reading).

Results

Once the test was completed, the average and standard deviation for each sample's readings was calculated. A standard function was obtained through linear logarithmic analysis of the 8 standards' values and their corresponding known PGD2 concentration. After determining the function through linear regression, a reverse x=f(y) analysis was sued to calculate the PGD2 concentration in each sample. After subtracting the background readings from the corresponding tube (*Ageratum conyzoides* solutions present a slight absorbance that may alter the test results, so corresponding solutions were analyzed and subtracted from each corresponding reading), the final PGD2 concentrations were compared to the uninhibited control in order to calculate the product's inhibition percentage.

Figure 9:
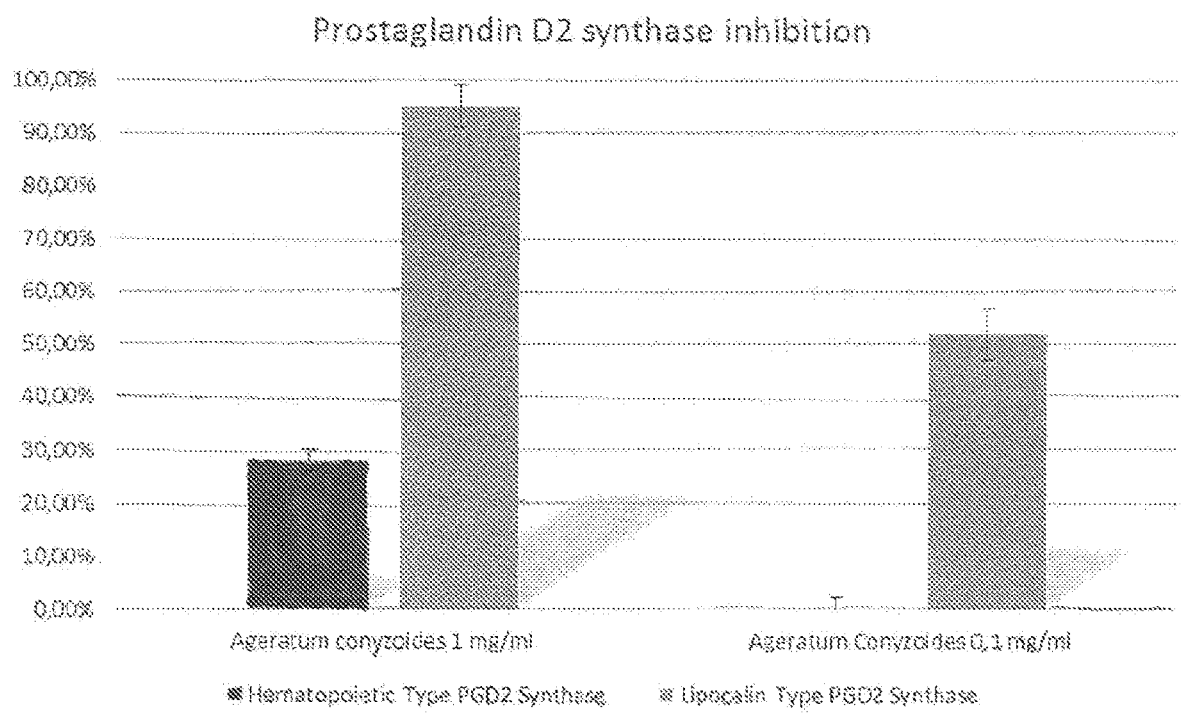
FIG. 9 is a graph showing the inhibition of Hematopoietic-Type PGD2 Synthase (HPGDS) (black bar to left) and Lipocalin-Type PGD2 Synthase (LPGDS) (grey bar to right) by an *Ageratum conyzoides* extract formulation according to this invention. Each enzyme tested at 1 mg/ml and 0.1 mg/ml.

The final concentrations and percentages of inhibition of PGDS are presented in Table 11 below, and illustrated in FIG. 9:

TABLE 11

Inhibition of Hematopoetic-Type PGD2 Synthase (HPGDS) and Lipocalin-Type PGD2 Synthase (LPGDS) by *Ageratum conyzoides* extract (±standard deviation)

| Sample | *Ageratum conyzoides* (1 mg/ml) | *Ageratum conyzoides* (0.1 mg/ml) |
|---|---|---|
| Hematopoietic-Type PGD2 Synthase (HPGDS) | 28.23% ± 1.95% | 0.00% ± 2.31% |
| Lipocalin-Type PGD2 Synthase (LPGDS) | 95.24% ± 4.07% | 52.15% ± 5.08% |

Conclusion

The *Ageratum conyzoides* extract (1 mg paste/ml) produced a very robust inhibition efficacy on the Lipocalin-Type PGDS enzyme in this method. The *Ageratum conyzoides* extract 1 mg/ml inhibited the Lipocalin-Type PGDS by about 95% as compared with control, thereby showing the *A. conyzoides* extract inhibits PGDS, and its production of PGD2, which inhibits hair growth. The 0.1 mg/ml *A. conyzoides* extract sample inhibited LPGDS by about 52%. Also, the 1 mg/ml *A. conyzoides* extract sample inhibited PGDS by about 28% as compared with control.

Example D

In Vitro Studies Showed Minimal to Slight Ocular Irritation by *Ageratum conyzoides* Extract SUMMARY: This test was designed to assess the ocular irritation potential of a non-surfactant, liquid article such as *Ageratum conyzoides* extract. The test is a modification of that described by Gautheron, et. al. ("Bovine Corneal Opacity and Permeability Test: An In Vitro Assay of Ocular Irritancy" Fund. Appl. Toxicol. 18:442-449 (1992)), and Vanparys, et al. ("Evaluation of the bovine opacity-permeability assay as an in vitro alternative to the Draize eye irritation test" Toxicol. In Vitro 7:471-76 (1994)).

This test used freshly obtained bovine corneas. Both opacity and permeability were measured. Values from both endpoints were used to obtain an in vitro score of 3.1. Using previously established criteria, the irritation potential of the *Ageratum conyzoides* extract test article was categorized as minimal or slight on the Draize Irritation Scale. (Gautheron et. al., 1994).

*Ageratum conyzoides* extract was tested for outer eye irritation potential by Bovine Corneal Opacity and Permeability assay, and was observed as having a very mild irritation only.

Materials and Methods:

Apparatus

Opacitometer (from MC2, Clermont, France)

Bovine cornea holders (from MC2, Clermont, France)

Spectrophotometer: A microplate reader capable of measuring optical densities at 490 and 570 nanometers (Dynatech MR 4000 Automatic Microplate Reader)

Water bath capable of 32° C.±2° C. (90° F.±4° F.)

Test Article and Controls

Test Article: *Ageratum conyzoides*

Positive Control Article: Ethanol—100%

Negative Control Article: Physiological saline

Test Procedure

Bovine eyes were obtained by this facility from a local abattoir. The eyes were transported in an appropriate container containing Hank's balanced salt solution (HBSS, Sigma Chemical Co., H-1387). Transportation and storage of the eyes was at approximately 21° C. (70° F.). The eyes were used the day of their harvest and transport.

Upon receipt, all eyes were examined. Magnification was used as needed. Eyes with corneas deemed unacceptable, due to scratches, vascularization, pigmentation, opacity, or for any reason, were discarded.

Accepted corneas were dissected from each eye, using a scalpel. A 2 to 3 millimeter wide piece of sclera was left surrounding the cornea. The corneas were placed in fresh HBSS until the testing began.

Upon test initiation, the iris and the lens were removed and the corneas were placed in the bovine cornea holders. The endothelial surface was applied to the O-ring of the posterior part of the holder. The anterior part of the holder was placed against the epithelial side of the cornea. The two sides of the holder were screwed together. The bovine holders' components were then filled with pre-warmed Eagle's Minimum Essential Media (EM EM, Sigma Chemical Co., M-3024) with 1% Fetal Bovine Serum (FBS, American Type Culture Collection) at approximately 32° C.±2° C. (90° F.±4° F.). The posterior chamber was filled first. The corneas were incubated for approximately one hour, in a 32° C.±2° C. (90° F.±4° F.) water bath. This allowed for the pre-equilibration of the corneas to the external medium.

During this pre-equilibration period, the opacitometer was calibrated, without a cornea, as per the operator's manual. The electrical zero (balance between photocells) was adjusted to "0" with the "bal." knob. The apparatus was set to "75" with a standardized opaque sheet of polyester, placed in the "positive" compartment.

After the pre-equilibration period, media from both of the chamber of the cassettes was aspirated, with the anterior chamber being aspirated first. Each chamber was then refilled with fresh EMEM, with the posterior chamber being filled first. Initial opacity readings were taken and recorded. Corneas with initial readings greater than 003 were not used. Three corneas were assigned to each test and control article. The corneas with the lowest readings were used as the negative controls.

The EMEM was then removed from the anterior chambers.

Opacity Measurement

The test article and the positive control article (ethanol) and the negative control article (physiological saline) were each tested at 100%.

A volume of 0.75 milliliters of the appropriate article, pre-warmed to 32° C.±2° C. (90° F.±4° F.), was introduced into the anterior chamber of the appropriate cassettes. The anterior chambers were then plugged and turned to a horizontal position. They were then rotated slightly, so that the article uniformly covered each cornea. The cassettes were incubated for 10 minutes at 32° C.±2° C. (90° F.±4° F.), in a water bath.

After the 10 minute exposure period, the articles were removed and the corneas were washed at least 3 times (or until the wash medium appeared clear). Each wash consisted of approximately 3 milliliters of EMEM being added to the anterior chambers via syringe. The media was removed with either a pipette tip or a flat ended needle. If an article could not be removed using this method the front cover of the cassette was removed and the cornea was then washed carefully, using a gentle stream of EMEM.

The anterior chambers of each cassette were then refilled with fresh EMEM via syringe. After refilling, the chambers were again plugged. All corneas were then incubated for 2 hours at approximately 32° C.±2° C. (90° F.±4° F.), in a water bath.

After this 2 hour incubation period, all compartments were emptied and refilled with fresh EMEM. Each holder was individually placed in the "positive" compartment, while the "negative" compartment was left empty. The glass portion of each holder was dried prior to the reading. The opacity of each cornea was taken and recorded. The corneas were also observed grossly. Any unusual findings, such as opaque spots, were recorded.

Permeability Determination

After the opacity readings were completed, the medium was removed from the anterior chambers. Either a suitable pipette tip or a flat ended needle was used for this procedure. One milliliter of 6 mg/ml fluorescein (Sodium Fluorescein, Sigma-Aldrich, F-637 in Dulbecco's Phosphate Buffered Saline (DPBS Sigma-Aldrich) pH approximately 7.5) solution was added to each of the anterior chambers. A micro pipette was used for this procedure.

After the fluorescein solution was added to each anterior compartment, the compartments were plugged. The cassettes were then incubated, in a horizontal position, for 90 minutes at 32° C.±2° C. (90° F.±4° F.), in a water bath. After the 90 minute incubation, the medium in the posterior chambers was mixed by drawing approximately 1 milliliter gently, up and down three times. A 1 milliliter syringe, with a small intubation needle, was used for this procedure.

A 200 microliter volume of the EMEM was then drawn from the posterior chamber of each cassette. The optical density ($OD_{490}$) of the EMEM sample was then measured spectrophotometrically, in a microplate reader at 490 nm, using 200 microliters of the fresh EMEM as the blank.

Results:

Tables 12 and 13 show results of the Bovine Corneal Opacity Assays described above.

change in opacity of each treated cornea (test article and positive control article) to obtain a corrected opacity.

The mean corrected corneal opacity value was determined from the individual, corrected opacity values of the corneas exposed to the test article and the positive control article.

Permeability—the corrected OD490 values (permeability) of the test article and the positive control article treated corneas were calculated by subtracting the average negative control cornea value from the original permeability value for each cornea.

The mean corrected permeability value of each treatment group was determined from the individual corrected permeability values of the corneas exposed to the test article and the positive control article.

The In Vitro Score for each individual test article and positive control article cornea was determined as follows: In Vitro Score=Corrected Corneal Opacity Value+(15×Corrected OD490 value). The mean In Vitro Score value for the test article and the positive control article was calculated from the individual In Vitro Score values.

The classification system shown in Table 14 was established by Gautherone et al. (1992) and refined by Vanparys et al. (1994). This system is intended to classify articles tested under standard conditions and is intended as a general guide. Results from test conditions should be compared to known articles tested under the same, or similar, conditions.

TABLE 12

Bovine Corneal Opacity Assay - *Ageratum conyzoides*

| Article | Cornea # | Initial Opacity | Terminal Opacity | Difference | Corrected Corneal Opacity | Mean Corrected Corneal Opacity |
|---|---|---|---|---|---|---|
| Test | 7 | 2 | 18 | 16 | 13.3 | 2.6 |
| Test | 8 | 0 | 0 | 0 | -2.7 | |
| Test | 9 | 0 | 0 | 0 | -2.7 | |
| +Control | 10 | 2 | 56 | 51 | 48.3 | 47.3 |
| +Control | 11 | 1 | 46 | 45 | 42.3 | |
| +Control | 12 | 1 | 55 | 54 | 51.3 | |
| −Control | 1 | 0 | 3 | 3 | — | — |
| −Control | 2 | 0 | 5 | 5 | — | |
| −Control | 5 | -1 | -1 | 0 (Average = 2.7) | — | |

TABLE 13

Bovine Corneal Permeability Assay - *Ageratum conyzoides*

| Article | Cornea # | Optical Density$_{490}$ | Corrected $OD_{490}$ | Mean Corrected $OD_{490}$ | In Vitro Score | Average In Vitro Score |
|---|---|---|---|---|---|---|
| Test | 7 | 0.076 | 0.070 | | 14.4 | 3.1 |
| Test | 8 | 0.016 | 0.010 | | -2.6 | |
| Test | 9 | 0.014 | 0.008 | 0.029 | -2.6 | |
| +Control | 10 | 1.239 | 1.233 | | 65.8 | 65.0 |
| +Control | 11 | 0.662 | 0.656 | | 52.5 | |
| +Control | 12 | 1.663 | 1.657 | 1.182 | 76.2 | |
| −Control | 1 | 0.009 | — | — | — | |
| −Control | 2 | 0.008 | — | — | — | |
| −Control | 5 | 0.002 (Average = 0.006) | — | — | — | |

Discussion

An In Vitro Score was determined from the opacity and permeability measurements.

Opacity—the difference in opacity value of each treated cornea (test article, positive control article, and negative control article) was calculated by subtracting the initial, basal opacity reading from the post treatment opacity reading. This value was determined for each cornea tested.

The average change in opacity for the negative control corneas was calculated. This value was subtracted from the

TABLE 14

Classification System

| Draize In vivo Score | Draize Irritation Scale | In vivo Score | In vivo Irritation Scale |
|---|---|---|---|
| 0-0.9 | Minimal | 0-3 | Non-irritating |
| 1-25 | Minimal/Slight | 3.1-25 | Mildly irritating |
| 26-56 | Moderate | 25.1-55 | Moderately irritating |
| 57-84 | Marked | 55.1-80 | Severely irritating |
| 85-110 | Extreme | >80.1 | Very severely irritating |

Under the conditions of this test, the test article, *Ageratum conyzoides* extract, at 100%, elicited an average in vitro score of 3.1. The positive control article, ethanol, at 100%, elicited an average in vitro score of 65.0. Therefore it is concluded that the test article, at 100%, is mildly irritating and would be expected to elicit a Draize in vivo score approaching 0, on a scale of 0 to 110. On the Draize Irritation Scale, the ocular irritation potential of the *Ageratum conyzoides* extract test article was categorized as minimal or slight.

Example E

SUMMARY: A Repeated Insult Patch Test (RIPT) was performed to determine the potential of *Ageratum conyzoides* extract of this invention to induce primary or cumulative irritation and/or allergic contact sensitization through repetitive epidermal contact. The RIPT test produced negative results with no irritation or allergic sensitization from repeated epidermal contact with the *Ageratum conyzoides* extract.

Clinical Information, Materials, and Methods:
Clinical Information
Participants: Fifty-seven (57) qualified subjects, male (18) and female (39), ranging in age from 16 to 77 years, were selected for this evaluation. Fifty-two (52) subjects completed this study. The remaining subjects discontinued the participation for various reasons, none of which were related to the application of the test material.
Inclusion Criteria:
 a. Male and female subjects, age 16 and over (with parental or guardian consent for age 16 year olds/minors).
 b. Absence of any visible skin disease which might be confused with a skin reaction from the test material.
 c. Prohibition of use of topical or systemic steroids and/or antihistamines for at least seven days prior to study initiation.
 d. Completion of a Medical History form and the understanding and signing of an Informed Consent form.
 e. Considered reliable and capable of following directions.
Exclusion Criteria:
 a. Ill health.
 b. Under a doctor's care or taking medication(s) which could influence the outcome of the study.
 c. Females who are pregnant or nursing.
 d. A history of adverse reactions to cosmetics or other personal care products.
Materials
Source Material: *Ageratum conyzoides*, Lot #ACZDS/321
Test Material: Prior to the initiation of this study, the Test Material was prepared. The Test Material of the below Example is a 2% dilution of the above Source Material, using distilled water as diluent.
Methods
Methodology: The upper back between the scapulae served as the treatment area. Approximately 0.2 ml of the Test Material, or an amount sufficient to cover the contact surface, was applied to the 1 inch×1 inch absorbent pad portion of a clear adhesive dressing. This was then applied to the appropriate treatment site to form a semi-occlusive patch.

Induction Phase: Patches were applied three (3) times per week (e.g., Monday, Wednesday, and Friday) for a total of nine (9) applications. The site was marked to ensure the continuity of patch application. Following supervised removal and scoring of the first Induction patch, participants were instructed to remove all subsequent Induction patches at home, twenty-four hours after application. The evaluation of this site was made again just prior to re-application. If a participant was unable to report for an assigned test day, one (1) makeup day was permitted. This day was added to the Induction period.

With the exception of the first supervised Induction Patch reading, if any test site exhibited a moderate (2-level) reaction during the Induction Phase, application was moved to an adjacent area. Applications were discontinued for the remainder of this test phase, if a moderate (2-level) reaction was observed on this new test site. Applications would also be discontinued if marked (3-level) or severe (4-level) reactivity was noted.

Rest periods consisted of twenty-four hours following each Tuesday and Thursday removal, and forty-eight hours following each Saturday removal.

Challenge Phase: Approximately two (2) weeks after the final Induction patch application, a Challenge patch was applied to a virgin test site adjacent to the original Induction patch site, following the same procedure described for Induction. The patch was removed and the site scored at the clinic twenty-four and seventy-two hours post-application.

Erythema and additional Dermal Sequelae were evaluated as shown in Table 15 below. Erythema was stored numerically. If present, additional Dermal Sequelae were indicated by the appropriate letter code and a numerical value set for severity.

TABLE 15

Evaluation Criteria

| Code | Description |
|---|---|
| 0 | No visible skin reaction |
| 0.5 | Barely perceptible |
| 1 | Mild |
| 2 | Moderate |
| 3 | Marked |
| 4 | Severe |
| E | Edema |
| D | Dryness |
| S | Staining |
| P | Papules |
| V | Vesicles |
| B | Bullae |
| U | Ulceration |
| Sp | Spreading |

The test described below was conducted in accordance with the Declaration of Helsinki, the ICH Guideline E6 for Good Clinical Practice, the requirements of 21 CFR Parts 50 and 56, other applicable laws and regulations, CPTC Standard Operating Procedures, and the approved protocol.

There were no adverse events, amendments, or deviations during this test.

Results:
Subject demographics and results for each subject are shown in Table 16. Observations remained negative throughout the test interval. All evaluations were "0", meaning no visible skin reaction was detected. No Dermal Sequelae were detected.

TABLE 16

Individual Results and Demographics

| Subject Numbers | Age | Sex | 24 hour* | Induction Phase 1 | 2 | 3 | 4 | 5 | 6 | 7 | 8 | 9 | Virgin Challenge Site 24 hr | Virgin Challenge Site 72 hr |
|---|---|---|---|---|---|---|---|---|---|---|---|---|---|---|
| 1 | 57 | M | 0 | 0 | 0 | 0 | 0 | 0 | 0 | 0 | 0 | 0 | 0 | 0 |
| 2 | 47 | M | 0 | 0 | 0 | 0 | 0 | 0 | 0 | 0 | 0 | 0 | 0 | 0 |
| 3 | 41 | F | 0 | 0 | 0 | 0 | 0 | 0 | 0 | 0 | 0 | 0 | 0 | 0 |
| 4 | 33 | F | 0 | 0 | 0 | 0 | 0 | 0 | 0 | 0 | 0 | 0 | 0 | 0 |
| 5 | 44 | F | 0 | 0 | 0 | 0 | 0 | 0 | 0 | 0 | 0 | 0 | 0 | 0 |
| 6 | 65 | F | 0 | 0 | 0 | 0 | 0 | 0 | 0 | 0 | 0 | 0 | 0 | 0 |
| 7 | 77 | M | 0 | 0 | 0 | 0 | 0 | 0 | 0 | 0 | 0 | 0 | 0 | 0 |
| 8 | 18 | M | 0 | 0 | 0 | 0 | 0 | 0 | 0 | 0 | 0 | 0 | 0 | 0 |
| 9 | 66 | F | 0 | 0 | 0 | 0 | 0 | 0 | 0 | 0 | 0 | 0 | 0 | 0 |
| 10 | 46 | F | 0 | 0 | 0 | 0 | 0 | 0 | 0 | 0 | 0 | 0 | 0 | 0 |
| 11 | 16 | F | 0 | 0 | 0 | 0 | 0 | 0 | 0 | 0 | 0 | 0 | 0 | 0 |
| 12 | 19 | F | 0 | 0 | 0 | 0 | 0 | 0 | 0 | 0 | 0 | 0 | 0 | 0 |
| 13 | 18 | M | 0 | 0 | 0 | 0 | 0 | 0 | 0 | 0 | 0 | 0 | 0 | 0 |
| 14 | 59 | F | 0 | 0 | 0 | 0 | 0 | 0 | 0 | 0 | 0 | 0 | 0 | 0 |
| 15 | 54 | F | 0 | 0 | 0 | 0 | 0 | 0 | 0 | 0 | 0 | 0 | 0 | 0 |
| 16 | 54 | F | 0 | 0 | 0 | 0 | 0 | 0 | 0 | 0 | 0 | 0 | 0 | 0 |
| 17 | 40 | F | 0 | 0 | 0 | 0 | 0 | 0 | 0 | $0^m$ | 0 | 0 | 0 | 0 |
| 18 | 29 | F | 0 | 0 | 0 | 0 | 0 | 0 | 0 | 0 | 0 | 0 | 0 | 0 |
| 19 | 23 | F | 0 | 0 | 0 | 0 | 0 | 0 | 0 | 0 | 0 | 0 | 0 | 0 |
| 20 | 50 | F | 0 | 0 | 0 | 0 | 0 | 0 | 0 | 0 | 0 | 0 | 0 | 0 |
| 21 | 45 | M | 0 | 0 | 0 | 0 | 0 | 0 | 0 | 0 | 0 | 0 | 0 | 0 |
| 22 | 45 | F | 0 | 0 | 0 | 0 | 0 | 0 | 0 | 0 | 0 | 0 | 0 | 0 |
| 23 | 44 | M | 0 | 0 | 0 | 0 | 0 | 0 | 0 | 0 | 0 | 0 | 0 | 0 |
| 24 | 27 | F | | DID NOT COMPLETE STUDY | | | | | | | | | | |
| 25 | 49 | M | | DID NOT COMPLETE STUDY | | | | | | | | | | |
| 26 | 17 | M | 0 | 0 | 0 | 0 | 0 | 0 | 0 | 0 | 0 | 0 | 0 | 0 |
| 27 | 42 | F | 0 | 0 | 0 | 0 | 0 | 0 | 0 | 0 | 0 | 0 | 0 | 0 |
| 28 | 18 | F | 0 | 0 | 0 | 0 | 0 | 0 | 0 | 0 | 0 | 0 | 0 | 0 |
| 29 | 54 | M | 0 | 0 | 0 | 0 | 0 | 0 | 0 | 0 | 0 | 0 | 0 | 0 |
| 30 | 48 | F | 0 | 0 | 0 | 0 | 0 | 0 | 0 | 0 | 0 | 0 | 0 | 0 |
| 31 | 43 | F | 0 | 0 | 0 | 0 | 0 | 0 | 0 | 0 | 0 | 0 | 0 | 0 |
| 32 | 17 | M | 0 | 0 | 0 | 0 | 0 | 0 | 0 | 0 | 0 | 0 | 0 | 0 |
| 33 | 20 | F | 0 | 0 | 0 | 0 | 0 | 0 | 0 | 0 | 0 | 0 | 0 | 0 |
| 34 | 64 | F | 0 | 0 | 0 | 0 | 0 | 0 | 0 | 0 | 0 | 0 | 0 | 0 |
| 35 | 17 | M | 0 | 0 | 0 | 0 | 0 | 0 | 0 | 0 | 0 | 0 | 0 | 0 |
| 36 | 40 | F | 0 | 0 | DID NOT COMPLETE STUDY | | | | | | | | | |
| 37 | 48 | F | 0 | 0 | 0 | 0 | 0 | 0 | 0 | 0 | 0 | 0 | 0 | 0 |
| 38 | 31 | M | 0 | 0 | 0 | 0 | 0 | 0 | 0 | 0 | 0 | 0 | 0 | 0 |
| 39 | 46 | M | 0 | 0 | 0 | 0 | 0 | 0 | 0 | 0 | 0 | 0 | 0 | 0 |
| 40 | 35 | F | 0 | 0 | 0 | 0 | 0 | 0 | 0 | 0 | 0 | 0 | 0 | 0 |
| 41 | 32 | F | 0 | 0 | 0 | 0 | 0 | 0 | 0 | 0 | 0 | 0 | 0 | 0 |
| 42 | 40 | M | 0 | 0 | 0 | 0 | 0 | 0 | 0 | 0 | 0 | 0 | 0 | 0 |
| 43 | 27 | F | 0 | 0 | 0 | 0 | 0 | 0 | 0 | 0 | 0 | 0 | 0 | 0 |
| 44 | 30 | F | 0 | 0 | 0 | 0 | 0 | 0 | 0 | $0^m$ | 0 | 0 | 0 | 0 |
| 45 | 42 | M | 0 | 0 | 0 | 0 | 0 | 0 | 0 | 0 | 0 | 0 | 0 | 0 |
| 46 | 52 | M | 0 | | DID NOT COMPLETE STUDY | | | | | | | | | |
| 47 | 18 | F | 0 | 0 | 0 | 0 | 0 | 0 | 0 | 0 | 0 | 0 | 0 | 0 |
| 48 | 63 | F | 0 | 0 | 0 | 0 | 0 | 0 | 0 | 0 | 0 | 0 | 0 | 0 |
| 49 | 49 | F | 0 | 0 | 0 | 0 | 0 | 0 | 0 | 0 | 0 | 0 | 0 | 0 |
| 50 | 28 | F | 0 | 0 | 0 | 0 | 0 | 0 | 0 | 0 | 0 | 0 | DID NOT COMPLETE STUDY | |
| 51 | 55 | F | 0 | 0 | 0 | 0 | 0 | 0 | 0 | 0 | 0 | 0 | 0 | 0 |
| 52 | 59 | M | 0 | 0 | 0 | 0 | 0 | 0 | 0 | 0 | 0 | 0 | 0 | 0 |
| 53 | 38 | F | 0 | 0 | 0 | 0 | 0 | 0 | 0 | 0 | 0 | 0 | 0 | 0 |
| 54 | 40 | F | 0 | 0 | 0 | 0 | 0 | 0 | 0 | 0 | 0 | 0 | 0 | 0 |
| 55 | 49 | F | 0 | 0 | 0 | 0 | 0 | 0 | 0 | 0 | 0 | 0 | 0 | 0 |
| 56 | 19 | M | 0 | 0 | 0 | 0 | 0 | 0 | 0 | $0^m$ | 0 | 0 | 0 | 0 |
| 57 | 16 | F | 0 | 0 | 0 | 0 | 0 | 0 | 0 | 0 | 0 | 0 | 0 | 0 |

*Supervised removal of 1st Induction and Challenge Patch at 24 hours.
$^m$Additional makeup day granted.

Discussion

Under the conditions of this study, the Test Material, *Ageratum conyzoides* Lot #ACZDS/321 did not indicate a potential for dermal irritation or allergic contact sensitization. With reference to Evaluation Criteria set out in Table 15 above, Table 16 shows that all datapoints read "0", meaning that no viable skin reaction was seen on any of the 55 subjects evaluated according to this study. Also, no Dermal Sequela was observed in any subject, and so no E, D, S, P, V, B, U, or Sp is noted in Table 16.

The use of the terms "a," "an," "the," and similar referents in the context of describing the present invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%; in other embodiments, the values may range in value above or below the stated value in a range of approximately ±5%; in other embodiments, the values may range in value above or below the stated value in a range of approximately ±2%; in other embodiments, the values may range in value above or below the stated value in a range of approximately ±1%. The preceding ranges are intended to be made clear by context, and no further limitation is implied. All method steps described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise stated. No language in the specification should be construed as indicating any non-claimed element as essential to the practice of the invention.

While in the foregoing specification the present invention has been described in relation to certain embodiments thereof, and many details have been put forth for the purposes of illustration, it will be apparent to those skilled in the art that the invention is susceptible to additional embodiments and that certain of the details described herein can be varied considerably without departing from the basic principles of the invention.

The present invention may be embodied in other specific forms without departing from the spirit or essential attributes thereof, and, accordingly, reference should be made to the appended claims, rather than to the foregoing specification, as indicating the scope of the invention.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

We claim:

1. An herbal preparation using herbaceous plants, *Ageratum conyzoides*, comprising: an herbal *Ageratum conyzoides* extract wherein said preparation comprises not less than 15% w/w saponins, not less than 8% w/w terpenes, not less than 2% w/w tannins, not more than 5 ppm lead as Pb, not more than 1 ppm Cadmium as Cd, not more than 3 ppm Arsenic as As, and not more than 1 ppm Mercury as Hg.

2. The herbal preparation of claim 1, wherein said preparation is a paste or a powder.

3. The herbal preparation of claim 2, wherein said herbal preparation comprises 16.3% saponins, 8.8% terpenes, and 2.3% tannins.

4. The herbal preparation of claim 2, wherein said preparation is water-soluble.

5. The herbal preparation of claim 1, wherein said herbal preparation further comprises a carrier and/or a diluent.

6. The herbal preparation of claim 4, further comprising an aqueous diluent mixed with the paste or powder.

7. The herbal preparation of claim 4, wherein said preparation is a shampoo.

8. The herbal preparation of claim 1, wherein said preparation is for topical application to skin.

9. A process for preparing an herbal preparation of claim 1 containing *Ageratum conyzoides*, comprising the steps of:
  a. providing pieces of *Ageratum conyzoides*,
  b. adding extraction solvent to the *Ageratum conyzoides* pieces to extract compounds from the pieces to prepare an herbal extract,
  c. removing the extraction solvent, and optionally removing the *Ageratum conyzoides* pieces from the herbal extract to prepare concentrated material, and
  d. formulating the concentrated material into an herbal extract formulation.

10. The process of claim 9, further comprising after step b and before step d, pooling the herbal extract with a second herbal extract using a second solvent to prepare concentrated material.

11. The process of claim 9, wherein said *Ageratum conyzoides* pieces are in powder form.

12. The process of claim 10, wherein said extraction solvent in steps b and c is methanol.

13. The process of claim 10, wherein said extraction solvent in steps b and c is ethanol.

14. The process of claim 10, wherein said pooling step comprises pooling an ethanol herbal extract with a methanol herbal extract to prepare a concentrated material.

15. The process of claim 14, wherein said formulating step d further comprises combining aqueous solution with the concentrated material and optionally filtering the resultant aqueous suspension to prepare an aqueous liquid herbal extract formulation.

16. The process of step 14, wherein said formulating step d further comprises dissolving the concentrated material in vegetable oil or propylene glycol/phospholipid and optionally filtering the resultant suspension to prepare an oil herbal extract formulation.

17. The process of step 14, wherein said formulating step d further comprises dissolving the concentrated material in a small quantity of ethanol in order to form a gel herbal extract formulation.

18. The process of claim 9, further comprising formulating the concentrated material into a shampoo.

19. A method of stimulating hair growth in a subject, comprising the steps of:
  a. providing an herbal preparation of *Ageratum conyzoides* according to claim 1, and
  b. applying the herbal preparation to the external surface of the skin of the subject.

20. A method of controlling hair fall in a subject, comprising the steps of:
  a. providing an herbal preparation of *Ageratum conyzoides* according to claim 1, and
  b. applying the herbal preparation to the external surface of the skin of the subject.

21. A method of controlling dandruff and related infections in a subject, comprising the steps of:
  a. providing an herbal preparation of *Ageratum conyzoides* according to claim 1, and
  b. applying the herbal preparation to the external surface of the skin of the subject.

* * * * *